United States Patent [19]
Little et al.

[11] Patent Number: 4,922,909
[45] Date of Patent: May 8, 1990

[54] VIDEO MONITORING AND REAPPOSITION MONITORING APPARATUS AND METHODS

[76] Inventors: James H. Little, 6601 S. Country Club Dr., Oklahoma City, Okla. 73159; William A. Lindgren, Rte. 4, Box 248, Rolla, Mo. 65401

[21] Appl. No.: 74,749

[22] Filed: Jul. 17, 1987

[51] Int. Cl.$^5$ .............................................. A61B 5/10
[52] U.S. Cl. .................................. 128/630; 128/774; 364/413.13
[58] Field of Search .............................. 128/630, 665; 364/413.13, 415; 382/6; 358/107, 110–113, 903; 33/512

[56] References Cited

U.S. PATENT DOCUMENTS

| | | | |
|---|---|---|---|
| 3,697,678 | 10/1972 | Belleson | 178/6.6 DD |
| 4,157,859 | 6/1979 | Terry | 350/35 |
| 4,214,267 | 7/1980 | Roese et al. | 358/111 |
| 4,429,960 | 2/1984 | Mocilac et al. | 351/212 |
| 4,459,990 | 7/1984 | Barnea | 128/656 |
| 4,497,024 | 1/1985 | Roth | 382/6 |
| 4,535,782 | 8/1985 | Zoltan | 128/665 |
| 4,594,608 | 6/1986 | Hatae et al. | 358/93 |
| 4,598,311 | 7/1986 | Bellina | 358/93 |
| 4,641,352 | 2/1987 | Fenster et al. | 382/6 |
| 4,665,437 | 5/1987 | Nicholson | 358/148 |
| 4,667,226 | 5/1987 | Glenn | 358/41 |
| 4,667,229 | 5/1987 | Cooper et al. | 358/98 |
| 4,669,466 | 6/1987 | L'Esperance | 364/413 X |
| 4,693,255 | 9/1987 | Beall | 128/665 x |
| 4,737,912 | 4/1988 | Ichikawa | 364/413 |

OTHER PUBLICATIONS

Hölme, H. K., "Digital Image Processing in Medicine", Springer–Verloy Publishing, N.Y., 1981, pp. 19–34 and 196.

*Primary Examiner*—Francis Jaworski
*Attorney, Agent, or Firm*—Senniger, Powers, Leavitt and Roedel

[57] ABSTRACT

Video monitoring apparatus for use in an application in which changes in relative spatial relationship of features of a biological tissue are to be observed. A video camera electronically produces a first image of the tissue and also electronically produces a subsequent image of the tissue after a period of time. A video display unit displays a representation of an image of the tissue derived from the camera. Circuitry connected to the camera and to the display unit electronically stores a representation of the first image of the tissue, and transmits the representation of the first image of the tissue to the display unit with a representation of the subsequent image of the tissue so that the first and subsequent images of the tissue appear superimposed. In this way, any differences in the relative spatial relationship of features in the images of the tissue are readily observed. A surgical reapposition monitor and methods are also disclosed.

20 Claims, 18 Drawing Sheets

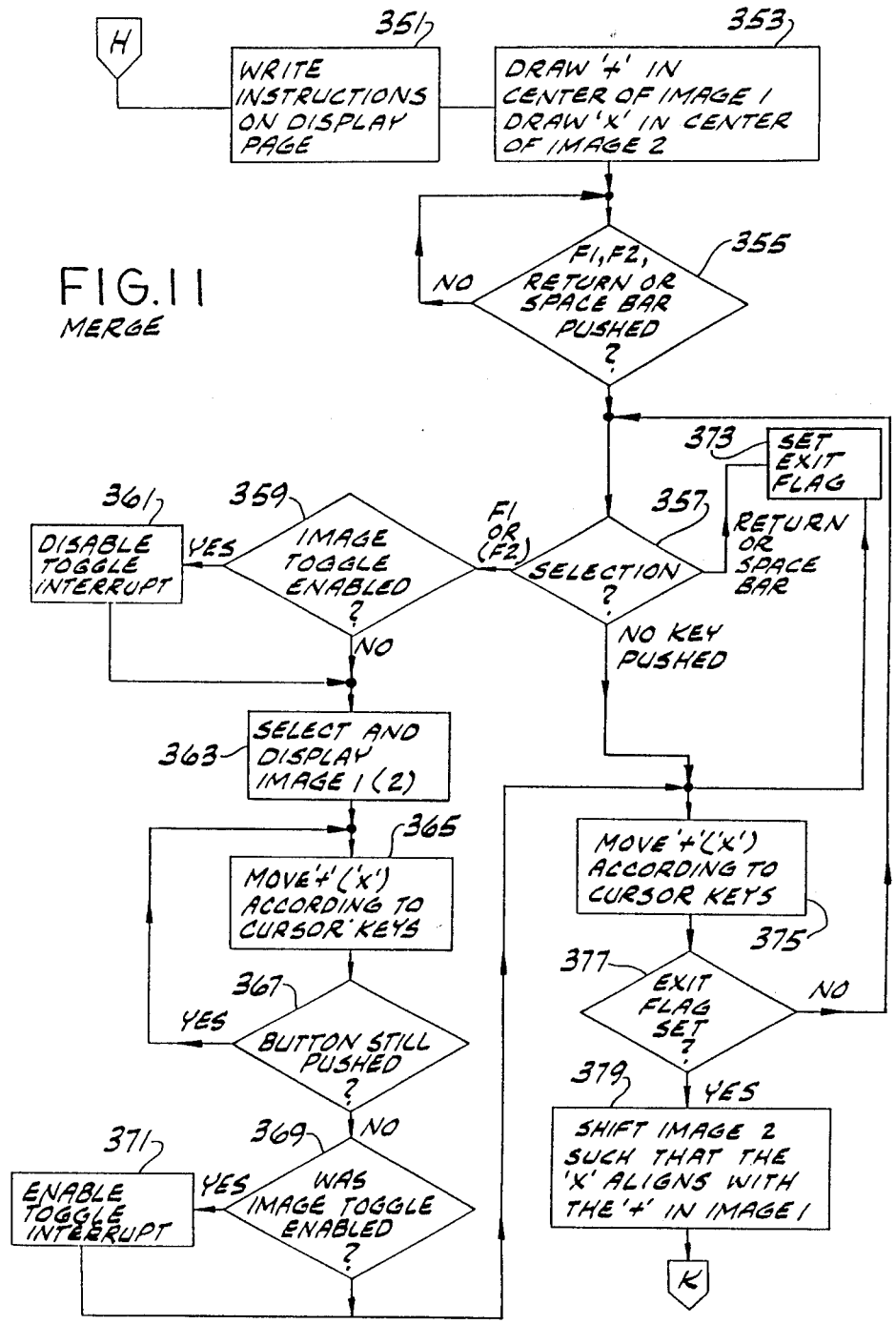

FIG.17
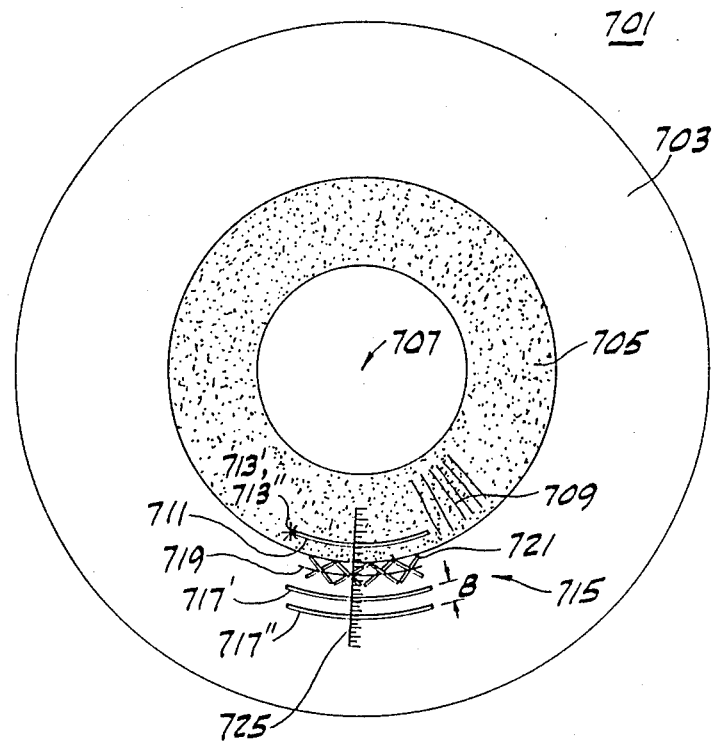
FIG.18 ALTERNATING
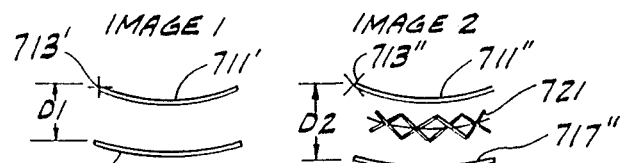
FIG.19
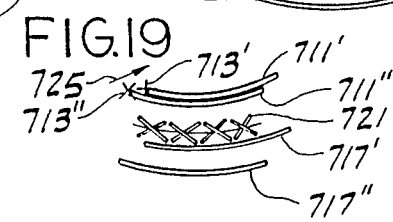

VIDEO MONITORING AND REAPPOSITION MONITORING APPARATUS AND METHODS

NOTICE

©1987 J. H. Little M.D. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

The present invention relates to video monitoring and reapposition monitoring apparatus and methods. More particularly, the present invention relates to monitoring apparatus and methods of video or other imaging technology for use in applications in which changes in relative spatial relationship of features of a biological tissue are to be observed, such as in surgical reapposition or closure of an incision and other medical or scientific procedures.

Without limiting the scope of the invention and its numerous intended applications, the background of the invention is described specifically in the context of eye surgery. During cataract surgery for example, it is desirable to close the incision so that when the eye heals the patient is left with a curvature of the cornea that either corrects pre-surgical astigmatism or avoids introducing astigmatism. Astigmatism occurs when one meridian of the cornea has a steeper radius of curvature than the median perpendicular to it.

Presently, the corneal curvature before surgery is measured and the meridian identified using an optical device called a keratometer, see for example U.S. Pat. Nos. 4,429,960 and 4,157,859. It has been known as a general matter that adjusting the suture tension and the healing process itself cause changes in astigmatism. A few days following surgery the eye is examined again using the keratometer. Depending on the results of the followup exam, the suture tension is adjusted so that when the eye has healed the astigmatism will be at least partially corrected. Because the value of corneal curvature determined by the keratometer depends on intracorneal pressure which the surgeon can only roughly restore by injection of fluid into the anterior chamber of the eye, and accuracy also depends on an absence of external pressures on the eye, the postoperative astigmatism value so determined is relatively uncertain at the conclusion of the operation and for a period of time thereafter. As a result, the patient's astigmatism may be only partially corrected, if at all.

It is believed that improvements are desirable in apparatus and methods for monitoring changes in relative spatial relationship of features of biological tissue such as in surgical reapposition and other medical or scientific procedures.

Two examples of prior art video monitors generally intended for use in the surgical operating room are disclosed in patent Nos. 4,598,311 and 4,594,608.

SUMMARY OF THE INVENTION

Among the several objects of this invention are to provide improved video monitoring and reapposition monitoring apparatus and methods which are convenient, accurate, and efficient to use in applications in which changes in relative spatial relationship of features of a biological tissue are to be observed; to provide improved reapposition monitoring apparatus and methods which enable a surgeon to close an incision accurately according to a predetermined criterion; to provide improved reapposition monitoring apparatus and methods which enable a surgeon to close an incision after eye surgery so that astigmatism is either substantially corrected or avoided in the process; to provide improved monitoring apparatus and methods which facilitate observation of changes in eye tissue due to glaucoma and of changes in the eye or other tissues due to other conditions; and to provide improved video monitoring and reapposition monitoring apparatus and methods which facilitate recordkeeping, and are relatively economical and reliable.

Generally, one form of the invention is video monitoring apparatus for use in an application in which changes in relative spatial relationship of features of a biological tissue are to be observed. A video camera system electronically produces a first image of the tissue and also electronically produces a subsequent image of the tissue after a period of time. A video display unit displays a representation of an image of the tissue derived from the camera. Circuitry connected to the camera system and to the display unit electronically stores a representation of the first image of the tissue, and transmits the representation of the first image of the tissue to the display unit with a representation of the subsequent image of the tissue so that the first and subsequent images of the tissue appear superimposed. In this way, any differences in the relative spatial relationship of features in the images of the tissue are readily observed.

In general, a method of the invention is used to monitor for changes in relative spatial relationship of features of a biological tissue. The method includes steps of electronically aligning a first video image of the tissue and a video image of the same tissue after a period of time has elapsed and automatically superimposing the video images for display purposes to allow the differences between the two images of the tissue to be easily distinguished.

Generally, another method of the invention is a surgical reapposition monitoring method including steps of electronically aligning pre-surgical and post-surgical video images and alternating them for display purposes to allow the differences between the two images to be easily distinguished.

In general, yet another method of the invention is a reapposition monitoring method for use in surgery wherein the position of pre-surgical tissue is to have a predetermined relationship to the position of the tissue after surgical incision and subsequent closure of the incision. Prior to surgery a surgical area on the patient is marked with marks located on opposite sides of an incision site and separated by a pre-surgical distance. A presurgical image of the marks and the incision site is electronically developed and stored. A post-surgical image of the marks and the incision site is electronically developed, and the post-surgical and pre-surgical images are superimposed on a display. Then there is measured on the images a value of difference between a pre-surgical distance between the marks and a post-surgical distance between the marks. The closure of the incision is adjusted until the value of difference between the pre-surgical distance and the post-surgical distance is substantially equal to a predetermined value.

Other objects and features will be in part apparent and in part pointed out hereinafter.

BRIEF DESCRIPTION OF THE DRAWINGS

FIG. 11 is a flowchart for superimposing visual reference points on two images and then sliding, shifting or aligning the images so that the reference points coincide according to operations of the menu of FIG. 2;

FIG. 17 is a pictorial diagram of a human eye in surgery as imaged by inventive monitoring apparatus according to inventive methods;

FIG. 18 is a sketch of pre-surgical and postsurgical images of sutures and an incision site on the eye of FIG. 17;

FIG. 19 is a sketch of the pre-surgical and postsurgical images of FIG. 18 superimposed on each other and to be aligned according to operations of FIG. 11;

Corresponding reference characters indicate corresponding parts throughout the several views of the drawings.

DETAILED DESCRIPTION OF PREFERRED EMBODIMENT

Figure 1:
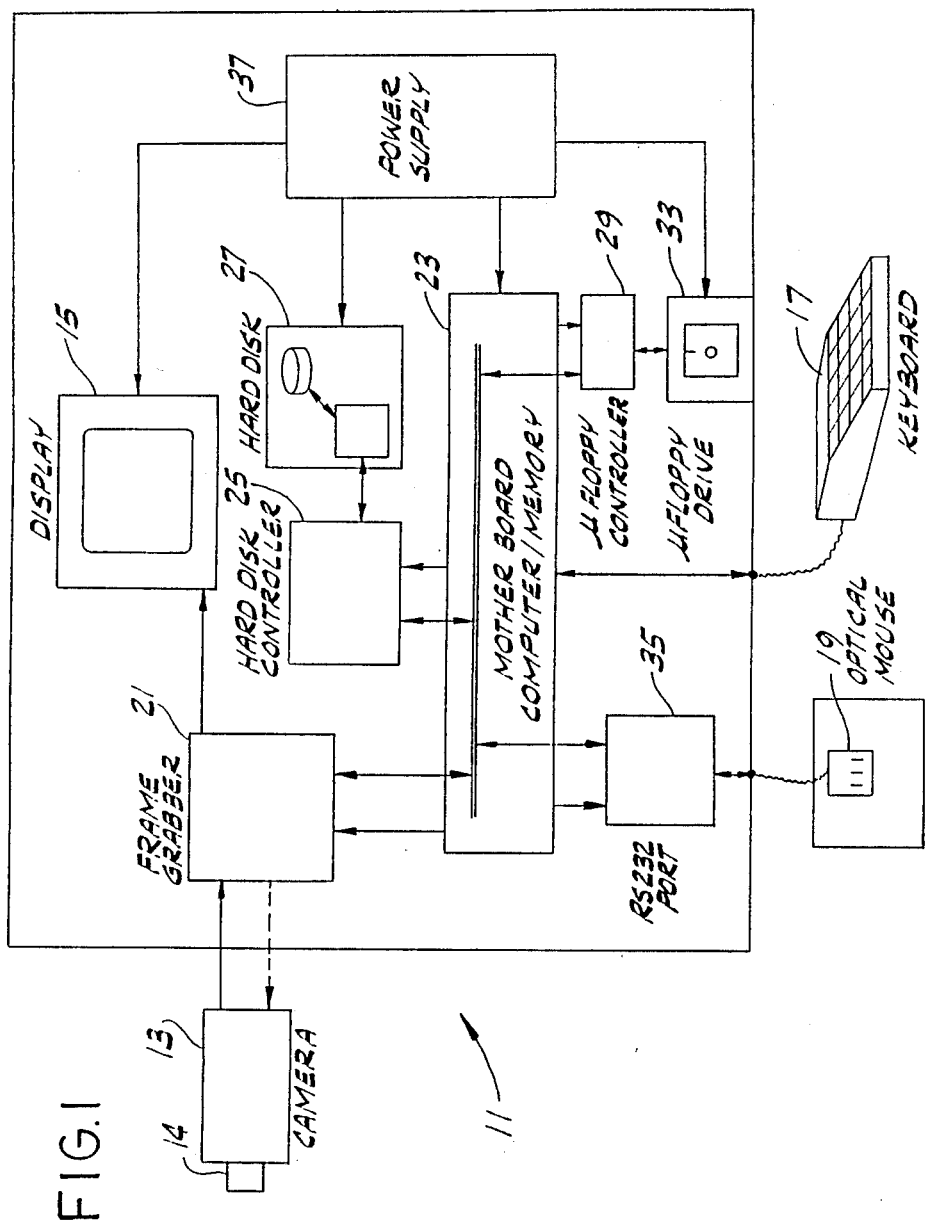
FIG. 1 is a block diagram of a video monitoring and reapposition monitoring apparatus of the present invention used in or operating according to methods of the present invention.

Advantageously, a system and methods of a preferred embodiment include hardware and software integrated together to provide a capability of alternately displaying an image acquired and displayed in real time and a stored reference image previously acquired and stored so that the two images are superimposed. In this way, an accurate assessment and/or correction of undesired physical distortion in the human eye during ophthalmic surgery, or other body parts in other procedures, or other specimens or objects in additional applications, is obtained.

Some applications of the apparatus and methods of the invention relate to comparing the position of human tissue before and after surgery, and more particularly to the position of eye tissue before and after cataract surgery using a high resolution camera with a computer system integrated to it.

A preferred embodiment of video monitoring and reapposition monitoring apparatus used in or operating according to the inventive methods has a personal computer and monitor equipped with a video processing, or frame grabber, circuit board. The accompanying software allows a presurgical image of the eye, with marking sutures, to be stored. After surgery is completed and the incision is being closed, the computer system aligns a present image of the eye with the stored image by overlaying a marking suture with the corresponding marking suture of the other image. In this way the surgeon can easily see the difference between the pre- and post-surgical images. The software provides a calibrated scale so that the differences between the images can quickly and accurately be measured. In this way the surgeon, equipped with the pre-surgical corneal curvature information and his cylinder regression profile, can immediately adjust the suture tension so that the eye heals back to the proper curvature with accompanying actual improvement in the patient's vision.

The computer-based image analysis monitor provides a comparative visualization of the position of presurgical tissue around an intended incision to its position after an incision, and during subsequent closure and suturing. Interactive imaging is obtained from a high resolution video camera mounted on a surgical microscope, and provides the cataract surgeon with apposition data to enable the optimal adjustment of suture tension for the control and reduction of astigmatism.

Before making the incision in ophthalmic surgery, but preferably after the conjunctival flap has been performed to anchor the eye and minimal cautery is applied using a bipolar eraser type cautery (e.g., Ocular Micro Systems bipolar cautery), interrupted lines of fine sutures are herein used to mark the tissue on or near the cornea, on each side and parallel to the intended incision. Microscope 14 is at full zoom, or highest magnification. A pre-incision image of this field is stored in the monitor's computer memory. One suture line acts as an anterior (corneal) marker, and the other as a posterior (scleral) marker. If a limbus base flap is used, the base of the flap may be used as the anterior marker, with a corneal marking suture omitted.

During closure of the incision, the monitor is used to acquire a real-time image. The stored pre-incision and real-time images of the marker sutures are compared using a flickered composite of the two to reveal any difference distinctly. The variance or difference B can be reduced or intentionally controlled by readjusting the suture tension for the appropriate cylinder regression. A built-in caliper or measurement scale enables precise measurement of this variance.

The pre- and post-operative images are archived in the internal storage system or on floppy disk for future reference.

In FIG. 1 monitor apparatus 11 has a video camera 13, a video display unit 15, a keyboard 17 and an optional optical mouse 19. ("Mouse" is a computer term for a handoperated input device connected by a cord to the computer and having buttons on a housing and a wheel sensitive to motion of the device along the table for entering numbers having values in a continuous range.)

Video camera 13 is a high resolution, high precision TV camera coupled to a surgical microscope 14 employed as an optical sensor to acquire highly magnified images of the portion of the eye involved in the surgery or other procedure. Camera 13 feeds video input to a Frame Grabber 21 which in turn connects both to display 15 and to a mother board holding a digital computer 23 such as an 8088 or 80286 chip with ROM (read only memory) and RAM (random access memory).

Frame Grabber 21 is a video board (such as the commercially available PFGPLUS-512-3-U-AT board from Imaging Technology, Inc.) that allows the computer to digitize video images received from camera 13 so that the images can be seen on display 15 and stored via a hard disk controller 25 on a hard disk 27 and/or via a microfloppy disk controller 29 on a floppy disk with a microfloppy drive 33. Thus, a high resolution image digitizer system is provided which records and stores into a digital memory, single TV frames of the images from the microscope of the intended sequentially acquired fields before, during and after surgery or otherwise.

Keyboard 17 is used by the operator to control and select the functions to be performed, or mouse 19 connected to computer 23 via an RS-232 port 35 may be used for many of the functions. Keyboard 17 has a standard IBM PC arrangement of its keys in which part of the keyboard has so-called function keys F1, F2, and so on, in addition to the alphanumeric keys of a standard typewriter keyboard. A power supply 37 is connected to the system components to power the hardware therein.

Software is suitably programmed in TURBO PASCAL, with IBM DOS operating system environment. In this way a microprocessor system is provided with software which manipulates the digitized images, discriminates and locates the desired measurement points, and provides precise measurements of the distances and distance differences between measurement points or marking sutures.

The terms "marking", "mark", and "marker" refer herein to original tissue features or added ink marks, points, lines, or marking sutures and the like which are detectable in any manner such as by visible light, infrared, ultraviolet, gamma rays, nuclear magnetic resonance or other procedures.

Figure 2:
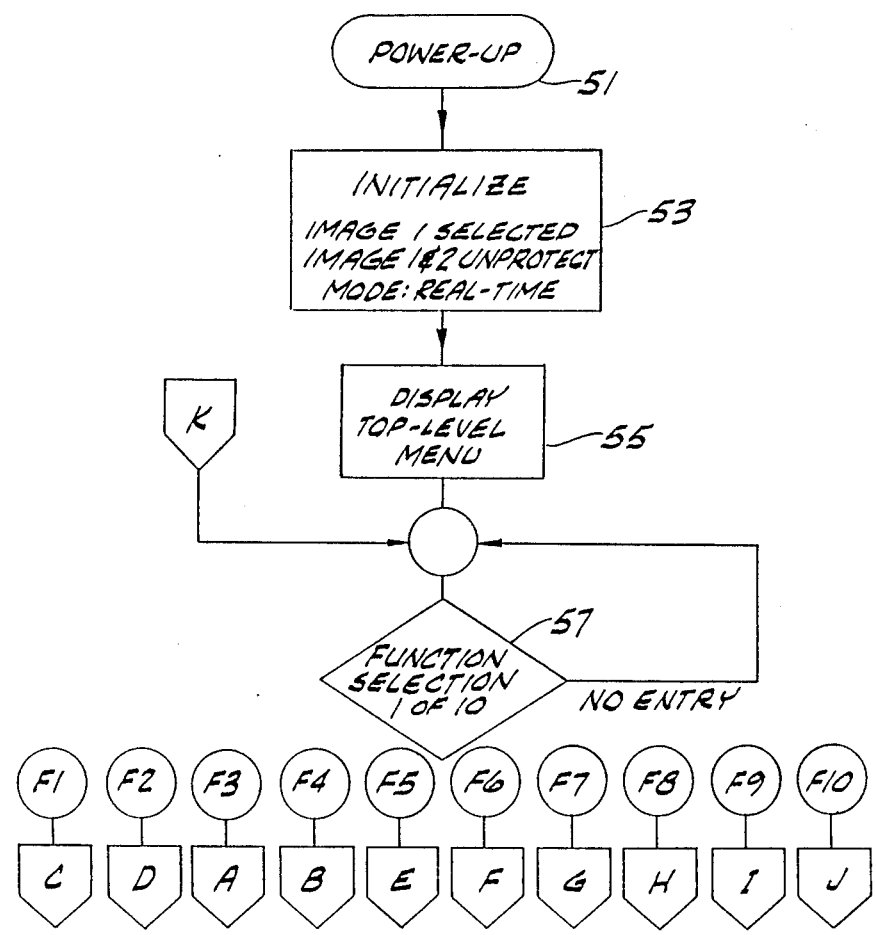
FIG. 2 is a flowchart of initialization and inventive menu operations of a computer in the apparatus of FIG. 1.

In FIG. 2, operations of the apparatus of FIG. 1 commence with a power-up step 51 and proceed to an initialization step 53. Step 53 selects a first image 1 for construction, and sets flags to indicate the image 1 and a second image 2 are unprotected. A mode designator is set for a Real Time mode (continuous monitoring of image sensed or produced by camera 13 through time). The real time image is digitized into two image memories (designated "IMAGE 1" and "IMAGE 2") and transmitted to and displayed from IMAGE 1 memory on the screen of display unit 15. Next, a step 55 is executed to display a main or top-level menu on the screen of display unit 15 showing ten operations. In a step 57 an operator selects one of the operations displayed on the menu by entry from keyboard 17 or mouse 19. The computer then jumps to one of ten points or paths A-J to execute one of ten functions F1-F10.

The selectable menu functions are listed on the following Main Menu Selections Table. Also displayed with the main menu are legends "PRESS BREAK FOR DISPLAY" and "SPACE AVAILABLE FOR_IMAGES" with the number of images filled in.

| MAIN MENU SELECTIONS | | |
| --- | --- | --- |
| Path | Function | Title |
| C | F1 | DISPLAY IMAGE 1 |
| D | F2 | DISPLAY IMAGE 2 |
| A | F3 | TOGGLE INPUT (REAL-TIME/FROZEN) |
| B | F4 | SIMULTANEOUS IMAGE DISPL. (ON/OFF) |
| E | F5 | MOVE DISPL. INTO BUFFER |
| F | F6 | STORE DISPL. AND/OR BUFFER ON DISK |
| G | F7 | RULER FUNCTIONS |
| H | F8 | JUXTAPOSE IMAGE |
| I | F9 | NAME FILE/PATIENT ID |
| J | F10 | FILE OPERATIONS AND CALIBRATION |

The FILE OPERATIONS AND CALIBRATION function F10 calls a Special Operations Menu listed as in the following table:

| SPECIAL OPERATIONS MENU | |
| --- | --- |
| F1 | LOAD DISPLAY AND/OR BUFFER FROM DISK |
| F2 | MODIFY GAINS AND OFFSETS |
| F3 | LIST IMAGES CURRENTLY ON HARD DISK |
| F4 | MOVE FROM HARD DISK TO PORTABLE DISK |
| F5 | MOVE FROM PORTABLE TO HARD DISK |
| F6 | RENAME STORED IMAGE |
| F7 | DELETE STORED IMAGE |
| F8 | SET TIME AND DATE |
| F9 | CALIBRATE RULER TO CAMERA OPTICS |
| F10 | RETURN TO MAIN MENU |

Figure 3:
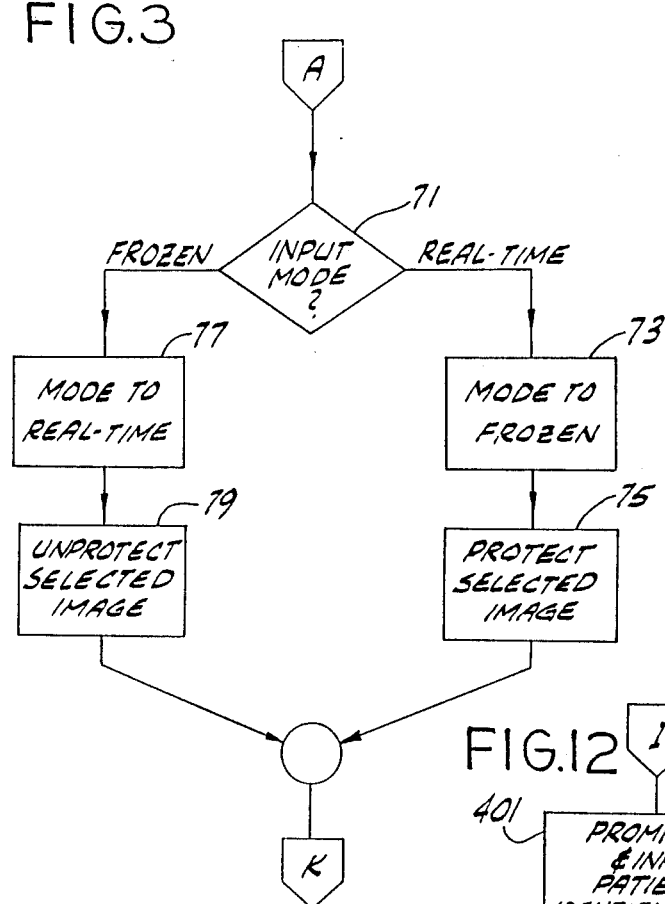
FIG. 3 is a flowchart of operations for a Frozen/Real-Time mode function of the menu of FIG. 2.

In FIG. 3, path A proceeds to an input and test step 71 which determines whether the mode is Real Time or Frozen. (The mode was originally initialized to Real Time in step 53 for continual display of events viewed by the camera 13.) A first selection of path A acts to freeze an image by changing the mode from Real Time to Frozen, and a next selection of path A acts to unfreeze the image by returning the system to Real Time mode.

If the mode is Real Time at test step 71, then operations proceed to a step 73 to change the mode flag to Frozen. In other words, if camera data is being continually digitized (Real Time mode), the digitization stops with the latest frame, thus freezing the display. A protection flag is also set in a step 75, which prevents the currently selected active image from being overwritten when it is subsequently no longer selected as the active image for display purposes.

If the mode is Frozen in test step 71, meaning that current camera data is not being digitized when path A function F1 is selected, then digitization resumes by action of a step 77 changing the mode from Frozen back to Real Time. Then a step 79 resets the protection flag so that a selected image can be overwritten with the latest real time image.

Pressing function key F3 of keyboard 17 is thus used to manually select path A in FIG. 3 to change from real time updating of the memory in Frame Grabber 21 to hold the current contents frozen and to freeze the image on display unit 15. Both memory areas IMAGE 1 and IMAGE 2 are affected. The current condition or mode is displayed by a message in capital letters on display unit 15.

Figure 7:
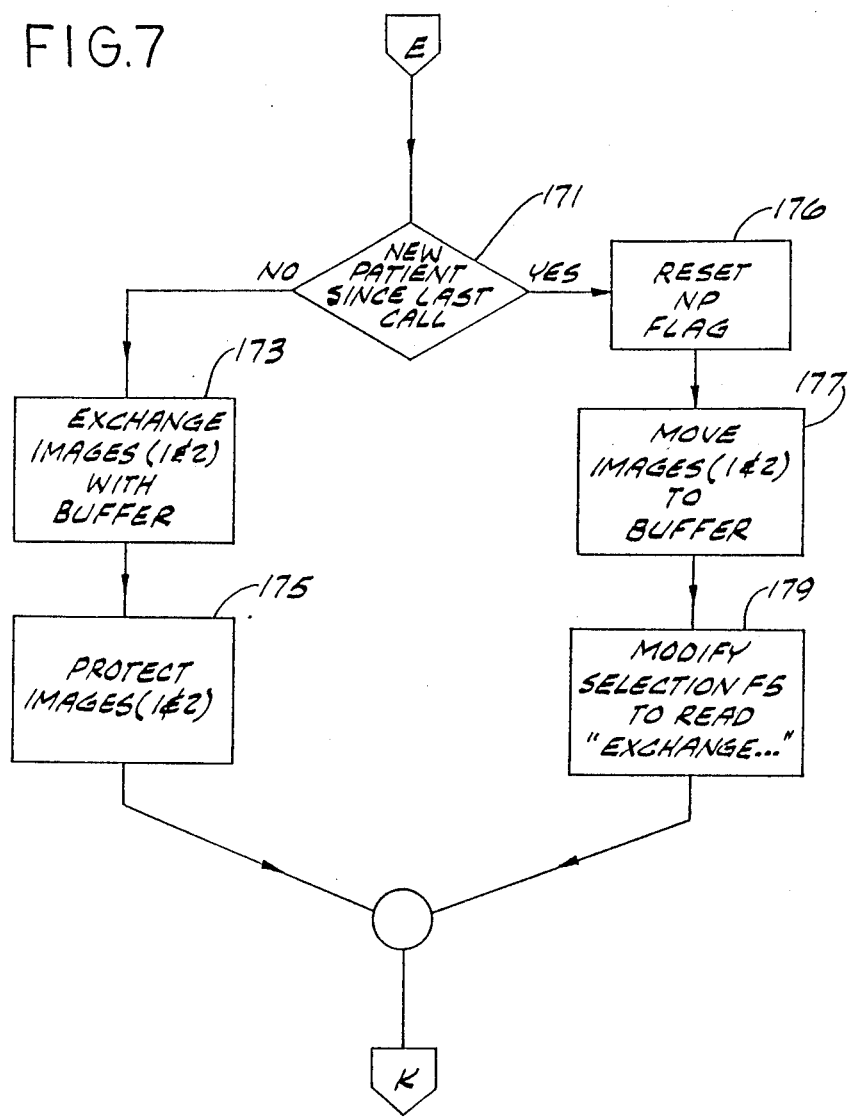
FIG. 7 is a flowchart of buffer operations of the menu of FIG. 2.

In addition to halting the display update which affects both images, changing the mode to Frozen applies protection to the image currently displayed. Conversely, changing back to Real Time mode removes this protection, except when a simultaneous display mode is selected (See FIG. 4). When protected, an image cannot be overwritten by incoming data and therefore appears frozen even when in Real Time mode. This allows alternate display of a realtime image and a still reference image. The protection flag or status is, however, ignored when a display is loaded from disk (FIG. 14, path JA) or accomplished by a buffer exchange (FIG. 7, Function F5, path E). Such a loading function is called a "display load." Thus, a protected image is overwritten by display loads from disk and buffer exchanges.

After execution of either step 75 or 79 in FIG. 3, operations proceed to a point K to loop back to step 57 of FIG. 2 whence the same function or another function can be selected by operator from the menu.

Figure 4:
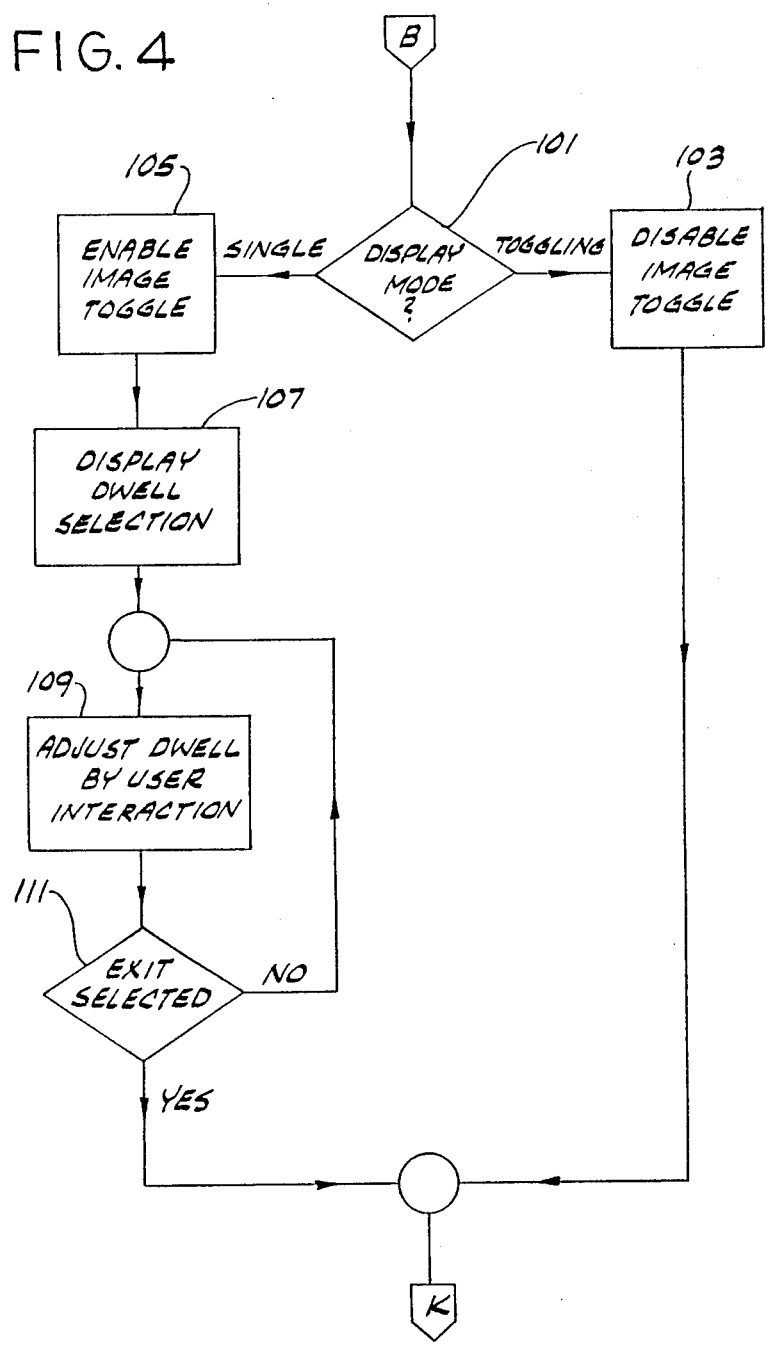
FIG. 4 is a flowchart of operations for a Single/Toggling mode including dwell adjustment for an alternating display function of the menu of FIG. 2.

In FIG. 4 selection of automatically alternating images or constant display of a single image is provided by path B, selected in step 57 by pressing function key F4. In a TOGGLE display mode, the operator has an opportunity to adjust the duration of each of two images which are displayed in alternating fashion. The dwell time of each image is adjusted independently to any value from 1/60 to 2.5 seconds duration. To adjust the dwell, a key on the keyboard designated by screen display for dwell adjust request is held and maintained depressed while operator also depresses a vertical up or down keyboard control key to increase or decrease the dwell time respectively. Software displays the duration time selected to the nearest 1/100 second on display unit 15. The display reads:

---

ADJUST TOGGLE RATE
DURATION OF DISPLAY:

IMAGE 1: 0.02 SEC. (hold F1 to adjust)
IMAGE 2: 0.02 SEC. (hold F2 to adjust)
DEPRESS SPACE BAR TO EXIT

---

Alternatively a button on the mouse 19 is held depressed to made the dwell adjust request, and then the mouse is moved to increase or decrease the dwell time.

In FIG. 4 operations of path B act as a software switch between the SINGLE or TOGGLE mode. Upon pressing function key F4, operations in a test step 101 determine whether a Single/Toggle flag is set for the TOGGLE or SINGLE mode. If the flag is set for the TOGGLE mode, operations proceed to a step 103 to disable the image toggle by resetting or switching the flag to the SINGLE mode, whence point K is reached and operations go to step 57 of FIG. 1. If in step 101 of FIG. 4 the flag were instead set for the SINGLE mode, then operations branch to a step 105 to enable the image toggle by setting the flag to the TOGGLE mode. In this way, an interrupt routine of FIG. 4B described hereinbelow is enabled to cause alternating display of images. Next, in a step 107, the dwell time for each image is displayed on unit 15. Then a step 109 senses the keyboard or mouse as described hereinabove, to adjust the dwell for one or both of the images as desired by operator until an exit signal is given by operator as sensed by a test 111. If the exit signal is not yet given, operations loop back to step 109 for further dwell adjusting. When the exit signal is given, operations proceed from step 111 to point K.

Figure 4A:
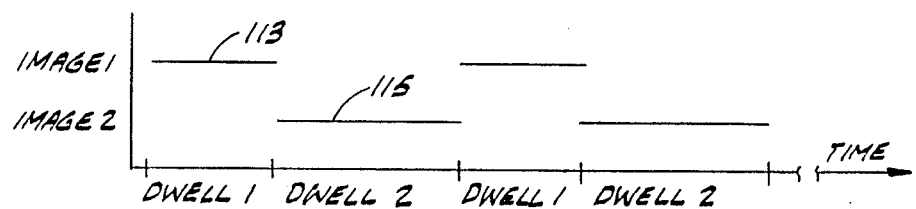
FIG. 4A is a graph of display status versus time indicating dwell times for first and second images resulting from operations of FIG. 4.

In FIG. 4A, Image 1 is displayed in toggle mode as represented by line 113 for a period of time DWELL1. Then Image 2 is displayed as represented by line 115 for a period of time DWELL2. Subsequently, display of Image 1 and then of Image 2 alternate over time, and display of either image is extended at the push of a button as described in connection with FIGS. 5 and 6 hereinafter.

Figure 4B:
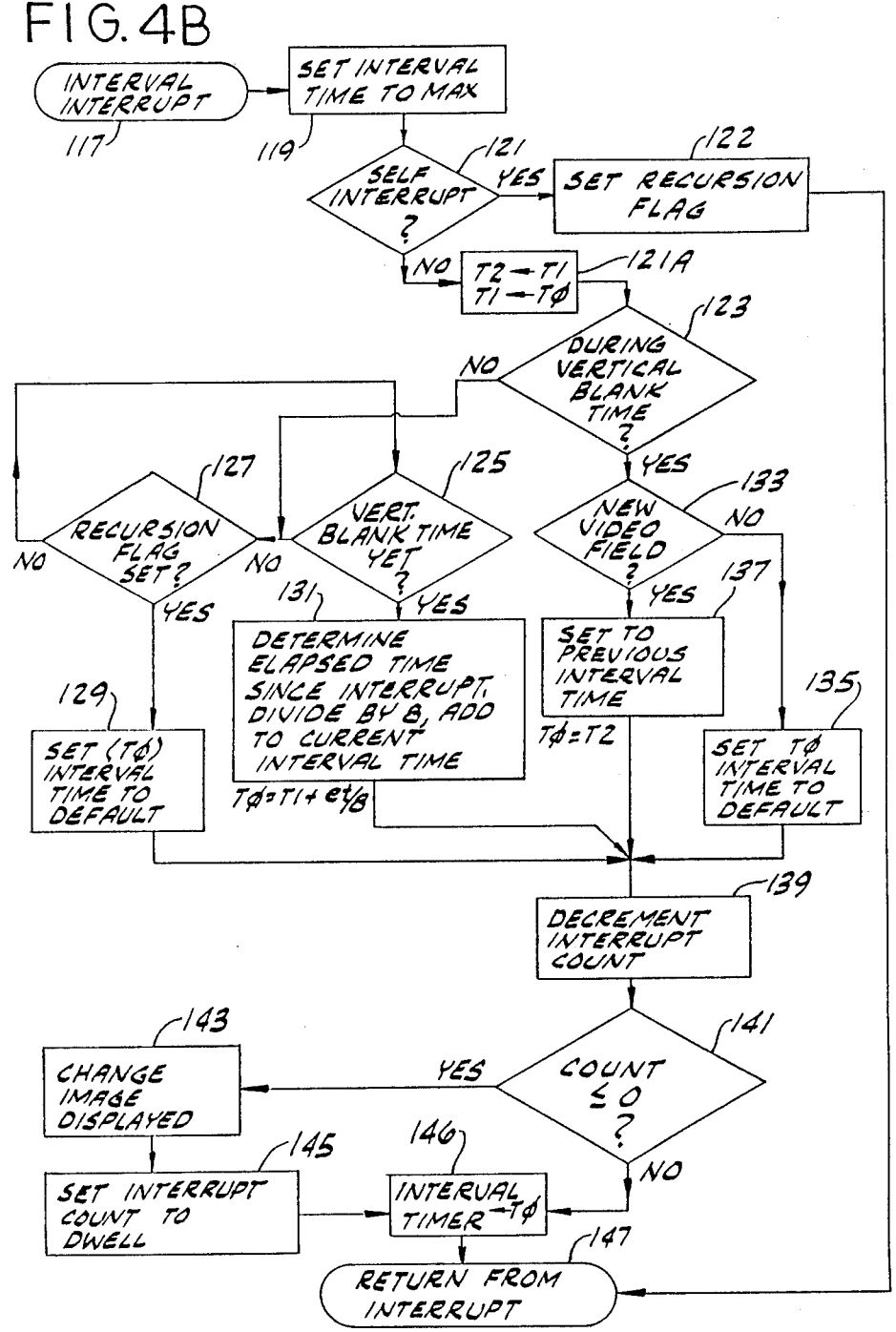
FIG. 4B is a flowchart of inventive operations of an interrupt routine for an alternating display function enabled by selection of the Toggling mode in FIG. 4.

In FIG. 4B an interval interrupt routine which allows the toggling of images 1 and 2 is shown. If the operator in FIG. 4 chooses the toggle mode the interval interrupt routine is enabled at regular intervals of time length T0 at an Interval Interrupt point 117. T0 is determined iteratively using its previous two values T1 and T2. Initially a step 119 resets the interval timer to a maximum (e.g., 53.3 milliseconds), and this allows more than enough time for the computer to complete the routine. A step 121 determines if there has been a self interrupt in the routine, if so a step 122 sets a recursion flag and the operations return from the interrupt routine. If in step 121 no self interrupt is detected, a step 121A updates the "last-two" values T2 and T1 and then a step 123 senses whether there is a vertical blank (frame grabber board just completed a sweep of the first or second field of a video frame). If time for a vertical blank is not detected in step 123 a step 127 determines whether the recursion flag is set, and if not operations will loop to step a 125 until time for a vertical blank. If the recursion flag is sensed in step 127 the new interval time T0 is set to a default value in a step 129. The default value is set somewhat less than 1/60 second, such as a counter value corresponding to 12.2 milliseconds.

When step 125 detects that it is time for a vertical blank, operations proceed to a step 131 which determines the elapsed time et since the interrupt started and divides this value by 8 and then adds this to current interval time T1 to determine a new value of interval T0. In this way the computer can self adjust to the time between vertical blanks so that the toggle can be accomplished on the front edge of a vertical blank. If step 123 detects a vertical blank, a step 133 determines if there is a new video field. If there is not a new video field, a step 135 sets the interval time T0 to the default value. If step 133 detects a new video field, a step 137 sets the new interval time T0 to the previous interval time T2, thus allowing the interrupt to happen on the front edge of a vertical blank.

Operations proceed from any of steps 129, 131, 135 or 137 to a step 139 which decrements the interrupt count once per interrupt, and a step 141 detects whether this count is now zero. When step 141 detects that the count has reached zero, a step 143 changes the image displayed. After step 143 a step 145 sets the interrupt count to a value representative of the dwell time established for the image now displayed. The interval timer is set to the new interval time T0 in a step 146 whence a Return from Interrupt point 147 is reached and operations return to whatever point in the main routine from which they were interrupted. Operations also reach step 146 when step 141 detects that the interrupt count has not reached zero. When step 122 has set the recursion flag, operations directly reach step 147.

Figure 5:
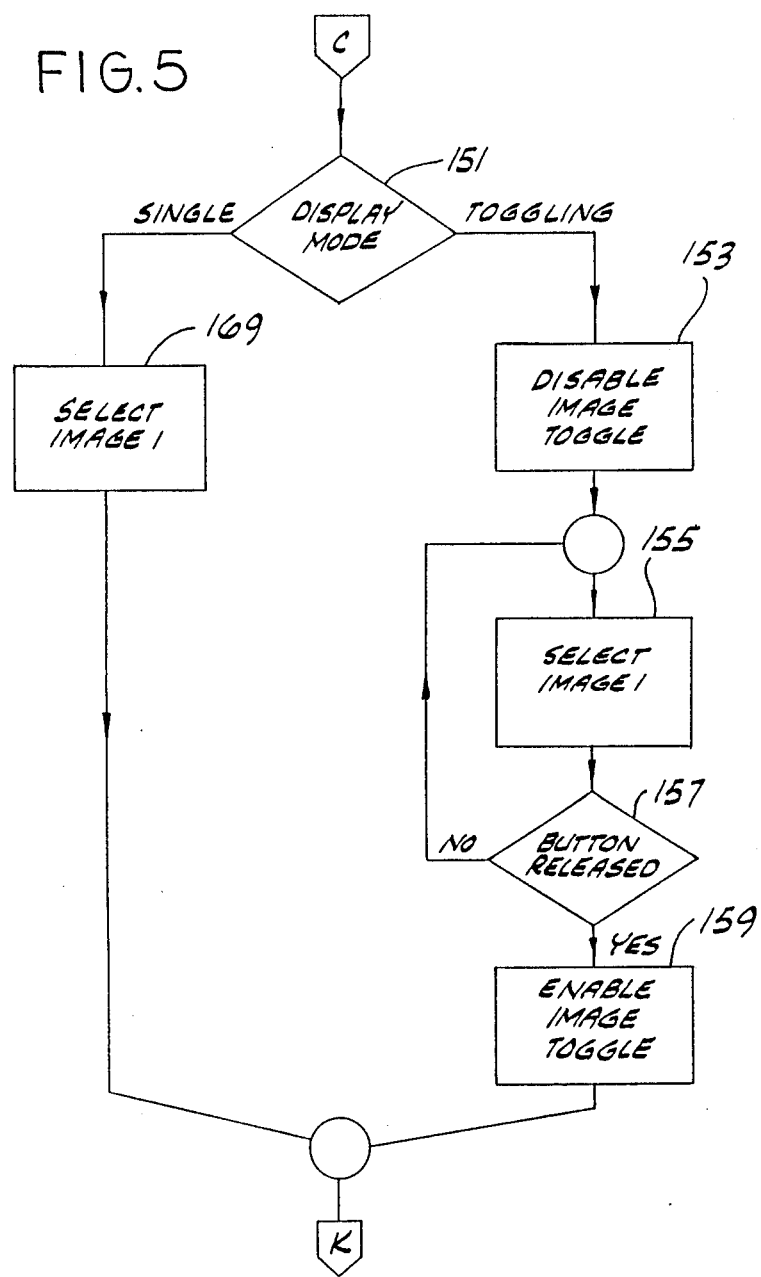
FIG. 5 is a flowchart of operations of an image selection function for a first image of the menu of FIG. 2.
Figure 6:
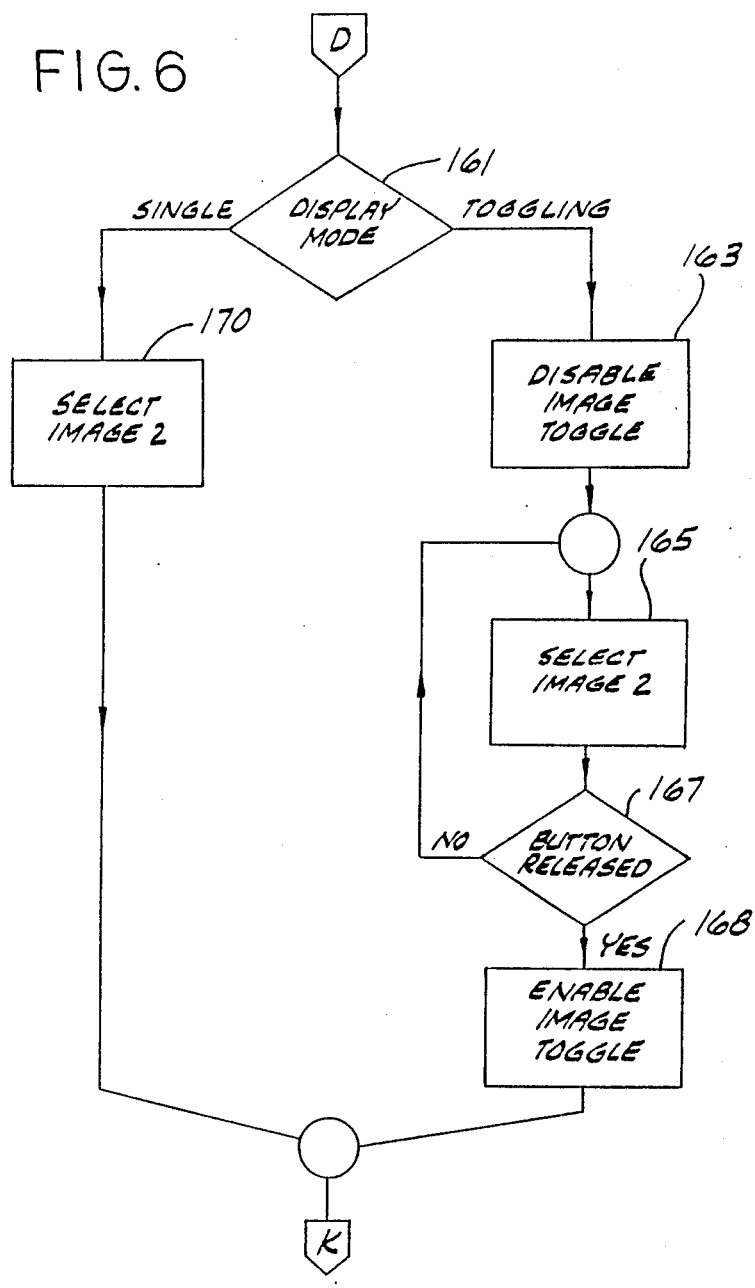
FIG. 6 is a flowchart of operations of an image selection function for a second image of the menu of FIG. 2.

FIGS. 5 and 6 paths C and D are selected by depressing function keys F1 and F2 respectively, and accomplish image select functions.

In FIG. 5 operations of path C in a step 151 determine whether the mode already established is SINGLE or TOGGLE. If the mode is TOGGLE, then operations proceed to a step 153 to disable the image toggle (resetting Single/Toggle flag to Single and thereby disabling interrupt routine of FIG. 4B). Next in a step 155, operations select IMAGE 1 memory and display the contents until a step 157 detects that the function key or button has been released. If not released, operations loop back to step 155 to extend the period of time during which the selected image is displayed. When the button is released, operations proceed from step 157 to a step 159 to set the image toggle to TOGGLE, thus enabling the interrupt routine of FIG. 4B, whence operations reach point K.

In FIG. 6 operations of path D in a step 161 determine whether the mode already established is SINGLE or TOGGLE. If the mode is TOGGLE, then operations proceed to a step 163 to disable the image toggle (resetting Single/Toggle flag to Single and thereby disabling interrupt routine of FIG. 4B). Next in a step 165, operations select IMAGE 2 memory and display the contents until a step 167 detects that the function key or button has been released. If not released, operations loop back to step 165 to extend the period of time during which the selected image is displayed. When the button is released, operations proceed from step 167 to a step 168 to set the image toggle to TOGGLE, thus enabling the interrupt routine of FIG. 4B, whence operations reach point K.

From the operator's point of view the system operates so that the image 1 or 2 selected by operations in FIG. 5 or 6 respectively is held on the screen for inspection until the key is released. When the key is released, the alternating display of IMAGE 1 and IMAGE 2 is resumed in TOGGLE mode due to the interrupt operations of FIG. 4B. In this way the computer and keyboard act as an example of means for sensing an operator selection of a particular one of the images and for holding only the selected image on the display by temporarily stopping the transmission of any other image.

If the system is not in the TOGGLE mode, the selected image is displayed until the TOGGLE mode is entered, or another image is selected. For example, in the SINGLE mode, if Image 1 is desired, operations enter path C of FIG. 5, and branch from step 151 to step 169 to display Image 1, after which point K of FIG. 2 is reached. Analogously, if Image 2 is desired, operations enter path D of FIG. 6, and branch from step 161 to step 170 to display Image 2, after which point K of FIG. 2 is reached.

In FIG. 7 selection of function key F5 causes operations to go to path E. Then a test step 171 checks new patient flag NP to determine whether there is a new patient (call to F9) since last call of function key F5. If not, operations proceed to a step 173 to exchange the contents of memory IMAGE 1 and IMAGE 2 with the buffer memory. This means that the latest images in VIDEO RAM are stored in the buffer RAM and the previously buffered images are brought up into VIDEO RAM. Next a step 175, the contents of IMAGE 1 and IMAGE 2 are put in a Protect status.

In step 171, if there is a new patient since last call of function key F5, operations proceed to a step 176 to set a New Patient (NP) flag and then to a step 177 to move or store the contents of memory IMAGE 1 and IMAGE 2 into the buffer memory. Then in a step 179, a flag for step 171 purposes is reset to the Exchange status so that unless there is another new patient (call to F9) before next access of function F5, operations will branch from step 171 to step 173 at that time. Put another way, if a subsequent operation is not the first selection of function F5 since a new patient name has been entered (F9 selected), an exchange takes place by which the contents of the buffer replace the current images. The display unit 15 also is made to display a legend that the contents of the buffer have been selected. After either step 175 or step 179, operations pass through point K back to FIG. 1 for selection of the next function.

Figure 8:
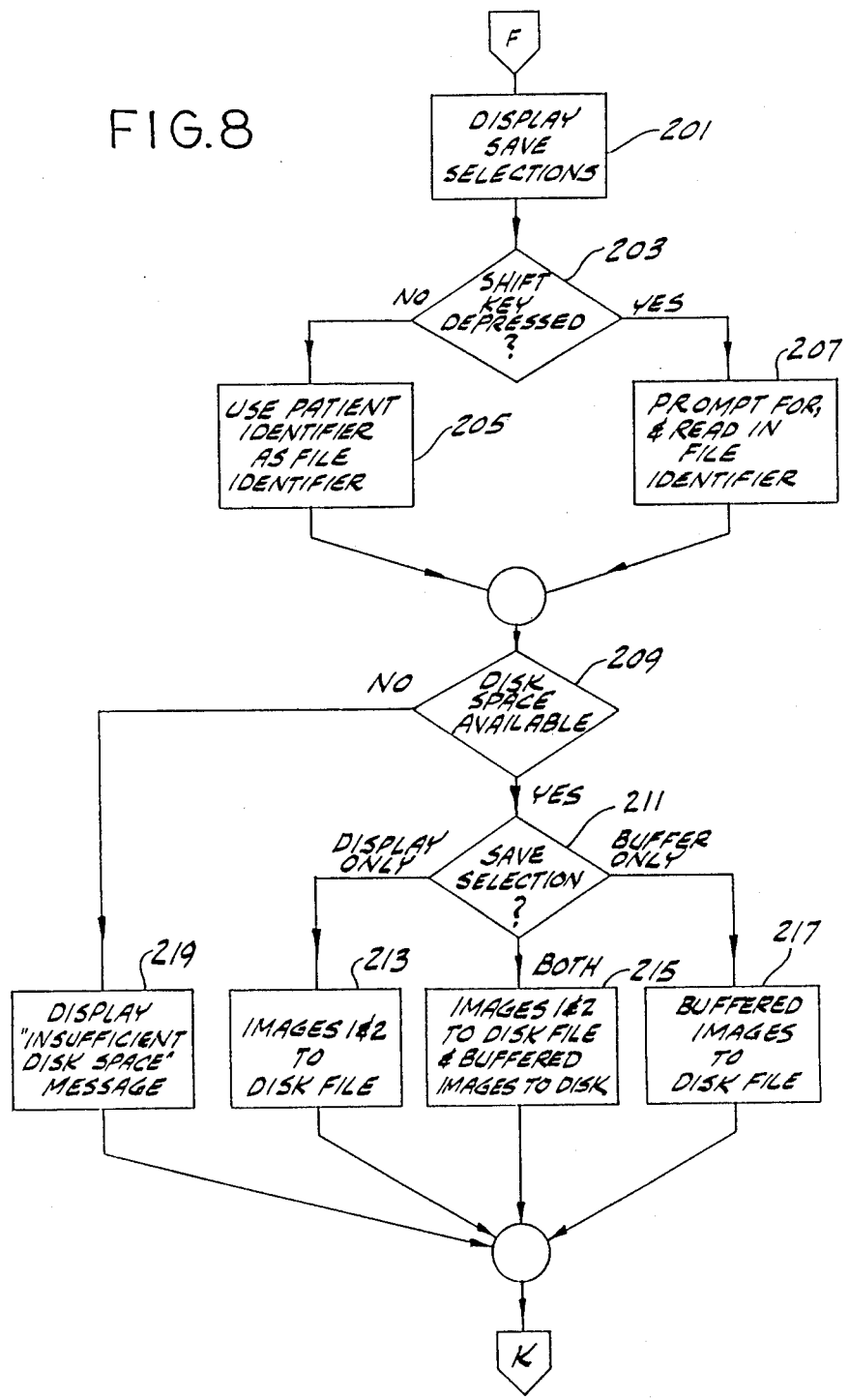
FIG. 8 is a flowchart of disk and recordkeeping operations of the menu of FIG. 2.

FIG. 8 illustrates operations accessed by function key F6 (path F), the STORE DISPLAY AND/OR BUFFER ON DISK selection. The user saves the current images and/or the current buffer to disk using this function. A submenu is displayed as follows:

| SAVE FILE SELECTION | | |
|---|---|---|
| Save Display F1 | Save Both Space Bar F2 | Save Buffer |
| HOLD SHIFT KEY TO OVERRIDE DEFAULTS | | |

In path F, key F1 is pressed to save display, space bar is pressed to save both display and buffer, and key F2 is pressed to save buffer only. File name(s) are optionally entered, and if they are not entered by operator then the current patient identifier with an appended qualifier, .n, is used as the file name(s).

Figure 12:
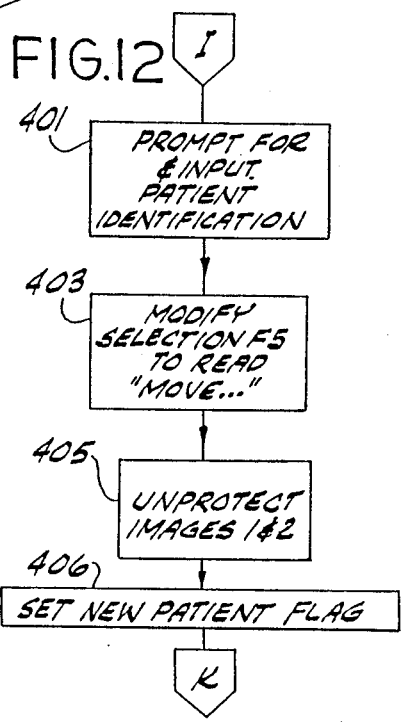
FIG. 12 is a flowchart for further buffer operations according to operations of the menu of FIG. 2.

Contents of either or both the display memory (IMAGE 1 and IMAGE 2) and the buffer are stored on disk, and the qualifier .n is incremented after each disk store operation. The patient identifier is specified by function F9 (FIG. 12, path I). The qualifier .n is reset to one (1) whenever a new patient identifier is specified. If a file exists with the same patient name, a second number #m is appended to the patient identifier ahead of the qualifier. If a file already exists with the second number #m appended, the appended #m is incremented and the qualifier .n is initialized to one.

The computer is programmed so that file names other than the default patient identifier are specified by holding the shift key on the keyboard depressed while the appropriate file name is entered. Escape from this and any other function is allowed at any time the disk is not being accessed. Escape is obtained by depressing the return key while holding a shift key in the depressed state.

In FIG. 8 operations in path F begin with a step 201 in which the computer displays a submenu of save selections or options: SAVE DISPLAY ONLY, SAVE BOTH DISPLAY AND BUFFER, and SAVE BUFFER ONLY. The display also invites the operator to depress shift key if a file identifier other than the patient identifier is to be input. Then in a step 203, a test is made to determine whether the shift key is depressed. If not, a step 205 automatically makes the patient identifier be the file identifier. If the shift key is depressed, a branch is instead made from step 203 to a step 207 which produces a prompt on the display unit 15 for input of a file identifier, and then reads in the operator-entered file identifier.

After either step 205 or 207 a test step 209 determines whether any disk space is available. Normally, there is space, and operations proceed to a step 211 to determine which Save Selection has been operator-entered in response to step 201. If the operator selection is SAVE DISPLAY ONLY, then operations go to a step 213 to save the contents of IMAGE 1 and of IMAGE 2 to disk. If the operator selection is SAVE BOTH DISPLAY AND BUFFER, then operations go to a step 215 to save the contents of IMAGE 1 and of IMAGE 2 and also the contents of the buffer to disk. If the operator selection is SAVE BUFFER ONLY, then operations go to a step 217 to save the contents to disk of the buffer only.

If in step 209, there is insufficient or no disk space found to be available, then a branch is made to a step 219 to output a message "Insufficient Disk Space" on display unit 15. After any of steps 213, 215, 217 and 219, operations reach point K and return to FIG. 1 where a new function is selected.

Figure 9:
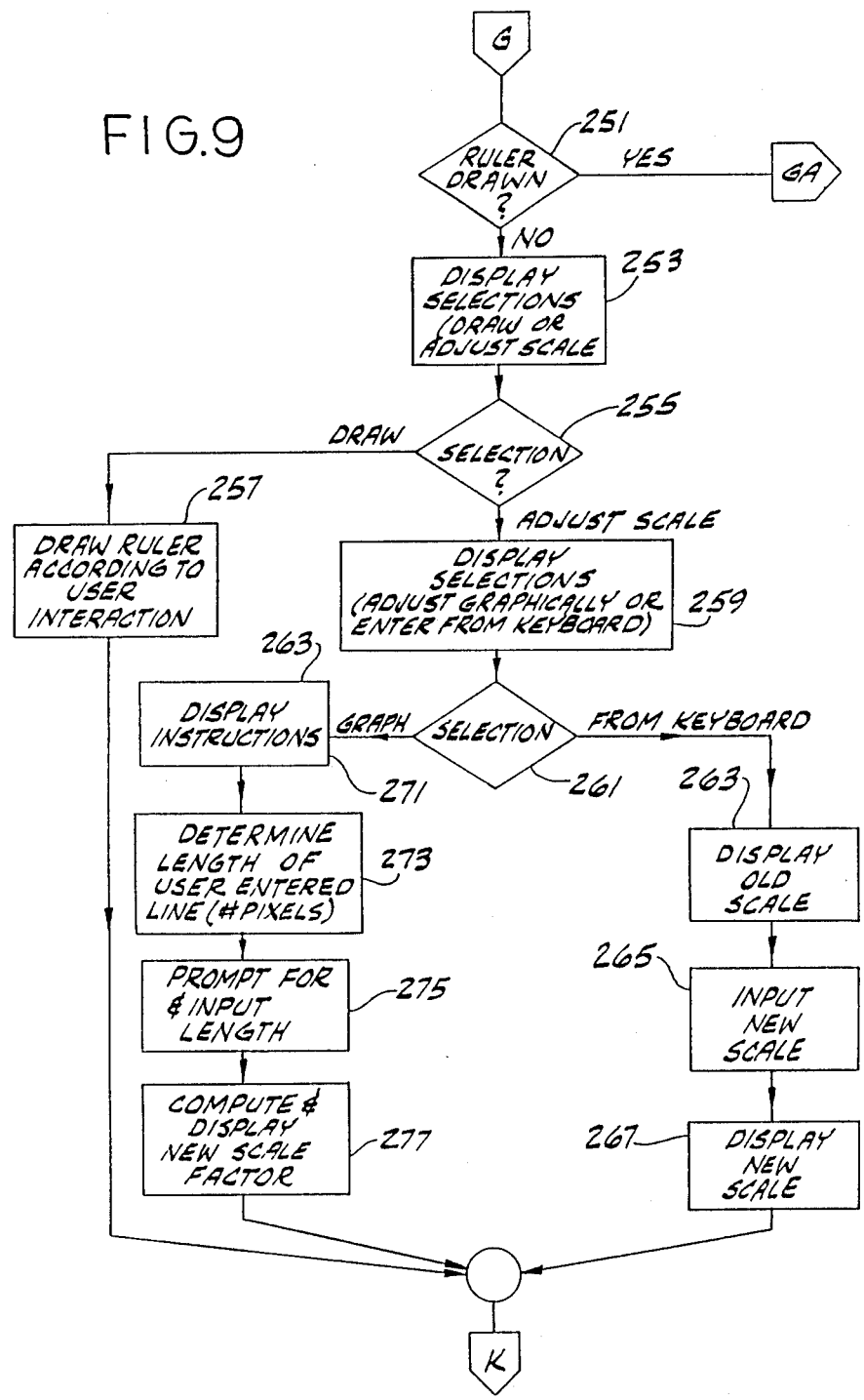
FIG. 9 is a flowchart for drawing or modifying a measurement scale or "software ruler" according to operations of the menu of FIG. 2.
Figure 10:
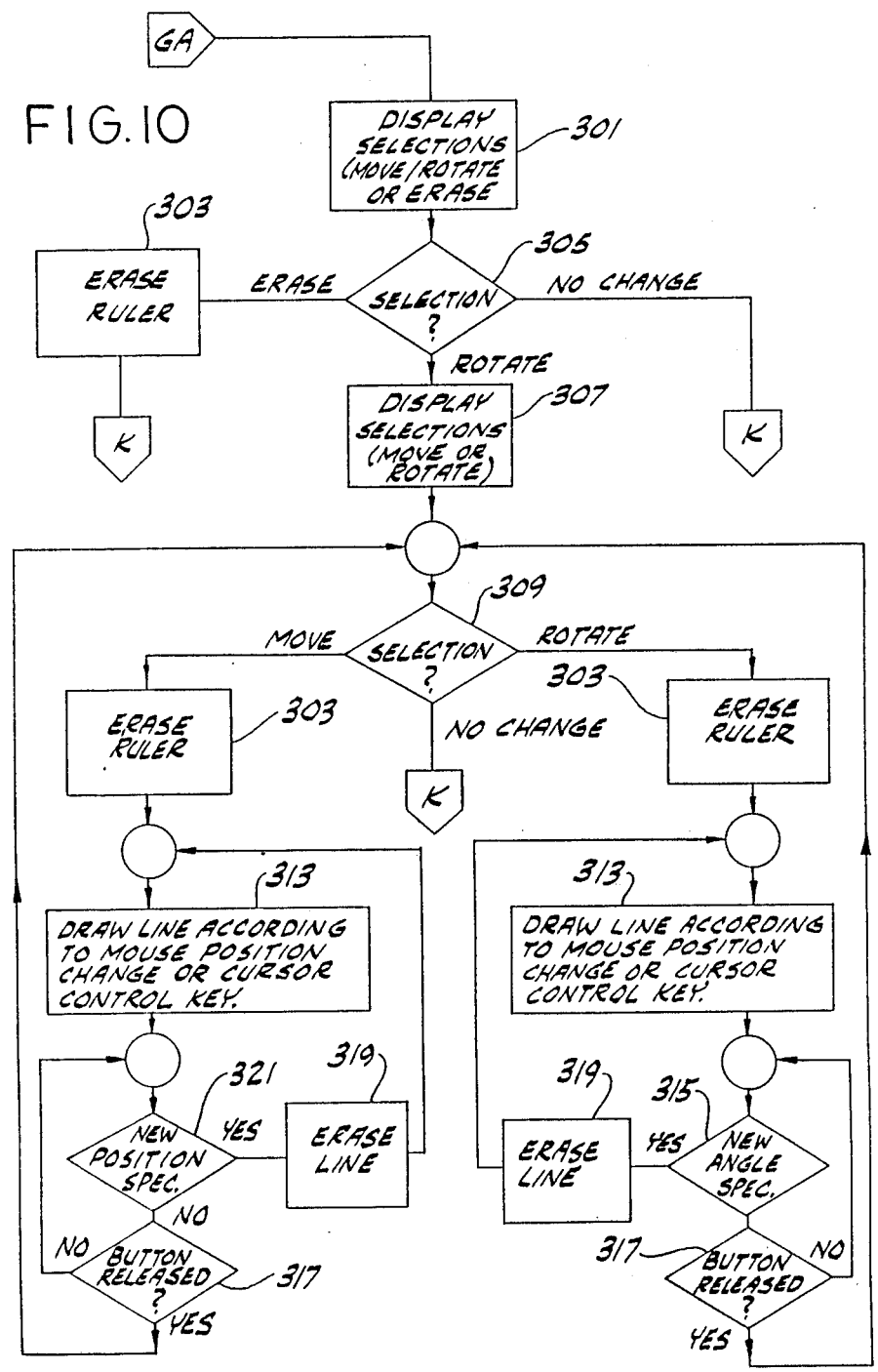
FIG. 10 is a flowchart for moving, rotating or erasing the measurement scale or software ruler according to operations of the menu of FIG. 2.

In FIG. 1, selection of software ruler function key F7 causes a branch from step 57 to path G of FIG. 9. If a ruler flag is set as determined in a step 251, meaning that a ruler is already drawn, path GA is followed as illustrated in FIG. 10. Otherwise, operations proceed from step 251 of FIG. 9 to a step 253 which displays options or selections entitled DRAW (key F1), ADJUST SCALING (key F2) AND NO CHANGE (space bar). In this way, if a ruler does not yet exist, the user chooses to draw one on the screen using cursor movement, or to change the scaling factor by entering a new scale factor directly, or tracing a line along a reference length. The ruler is useful for image measurements and comparisons. The units of the ruler are set when calibration is performed using special menu operation function F9 (path JI, FIG. 16). A scale factor for the ruler is also advantageously modified for use at different microscope magnifications.

To draw a ruler after selection of path G, depress and release F1 or the left mouse key, which selects the DRAW option at a step 255, from which operations branch to a step 257. The system draws a ruler vertically in the center of the screen of display unit 15. The ruler is drawn with a selected spatial interval of a unit such as millimeters. A wide tick mark is provided each unit length with subdivisions as narrower tick marks. The tick marks are referenced to one side of the ruler.

After the ruler is drawn, it is repositioned by depressing key F1 and the up, down, right or left cursor control keys or depressing the left mouse button and moving the mouse for X, Y (horizontal and vertical) positioning. The ruler is rotated by depressing and holding an additional key F2 and either the up or down cursor control key or depressing the right mouse button and moving the mouse to produce counterclockwise or clockwise rotation respectively. The ruler folds into a line before it is moved or rotated to the desired position.

If in step 255 operator selects the NEW SCALE SELECTION (Adjust Scale) option, operations go to a step 259 whereupon the computer displays further options DETERMINE GRAPHICALLY (key F2) or KEYBOARD ENTRY (key F1). A test step 261 determines the nature of the operator response. If the operator response is ENTER FROM KEYBOARD, then operations go to a step 263 to display the previous scale for the ruler, then request from operator and receive a new scale value in a step 265, and then display the new scale on the ruler in a step 267.

If the operator response in step 261 is ADJUST GRAPHICALLY, then operations go to a step 271 to display instruction for graphical adjustment of the ruler by requesting operator to enter a line having a length related to the unit of measurement of the scale being in effect requested. Operator enters the line by mouse or cursor control key operations. Then a step 273, determines the length in number of pixels on the screen of the user entered line. Next, a step 275 outputs a prompt to display unit 15 to request the length of the new ruler from the operator. Operator responds by mouse or control key. Then a step 277 computes and displays the new scale factor.

If from step 251 it has been determined that the ruler is drawn the operations go to FIG. 10 to a step 301 which displays selections entitled ERASE (Key F2), MOVE/ROTATE (Key F1), and NO CHANGE (Space Bar).

To erase the ruler, operator selects the ERASE option (F2 or right mouse) at a step 305, from which operations branch to a subroutine step 303 where the computer deletes the ruler and then branches to step 57. If operator selects the NO CHANGE option then the operations branch directly to step 57.

If at step 305 operator selects MOVE/ROTATE option, operations go to a step 307 whereupon the computer displays further options NO CHANGE (space bar or center mouse button), MOVE (F1 or left mouse button) and ROTATE (F2 or right mouse button). A test step 309 determines the nature of the operator response. If the operator response is NO CHANGE, then operations go directly to step 57.

If the operator response in step 309 is ROTATE, then operations go to subroutine step 303 to erase the ruler image. The software then draws a line corresponding to the angle and position of the ruler just erased, in a subroutine step 313. When the computer changes the ruler to a line, then with a step 315 the software checks to see if a new angle of rotation has been specified (i.e., the mouse has been moved or cursor control key depressed). If a new rotation angle has been specified by motion of the mouse or depressing cursor control key, then in a step 319 the line in the former position is erased and the line in the new position is drawn. If a new angle has not been specified in step 315 then a step 317 senses if the selecting key (F2 or right mouse key) has been released. If it has the operations go to step 309. If the selecting key has not been released the operations go back to step 315.

If the response in step 309 is MOVE, then operations go to a step 303 to erase the ruler image. Similar to the ROTATE option, next the software then draws a line corresponding to the angle and position, of the ruler just erased, in the subroutine step 313. When the line has been drawn in place of the ruler the software checks to see if a new position has been specified with a step 321. The position is specified by depressing the up, down, right or left cursor control keys or by motion of the mouse. If a new position has been specified a step 319 erases the line in the former position and the line in the new position is drawn in step 313. If a new position in step 321 has not been specified then a step 317 senses if the selecting key (F1 or left mouse button) has been released. If in step 317 it is sensed that the selecting key has been released the operations go to step 309. If the selecting key has not been released the operations go to step 321.

In FIG. 2, selection of JUXTAPOSE IMAGE (MERGE) function F8 causes a branch from step 57 to path H of FIG. 11. Operations of FIG. 11 proceed to a step 351 which displays instructions on how to proceed. The instructions read:

| IMAGE JUXTAPOSITION |
| --- |
| DEPRESS: F1 TO SELECT IMAGE 1; F2 TO SELECT IMAGE 2; SPACE BAR TO REPOSITION IMAGE THE X WILL BE POSITIONED UPON THE + |

Operations proceed to a step 353 in which a software '+' is drawn in the center of image 1 and a software 'x' is drawn in the center of image 2. A step 355 then senses if the F1, F2, Return or Space Bar keys have been pushed. If one of these keys has been pushed then operations proceed to a step 357 if not the software will loop step 355 until one of the above mentioned keys has been pushed. In a step 357 if either key F1 or F2 has been pushed operations proceed to a step 359 which determines if the image toggle is enabled.

If in step 359 image toggle is enabled a step 361 disables the toggle interrupt routine and operations go to a step 363. If the image toggle is already not enabled in step 359, operations go directly to step 363. Step 363 selects and displays image 1 or 2 depending on whether F1 or F2 has been pressed. Operations then proceed to a step 365, the operator moves the software '+' or 'x' reference points, depending on the image displayed, to the desired point of reference on the image according to cursor keys. A step 367 then determines if any of the cursor keys for moving the '+' or 'x' are still being moved. If so, operations loop back to step 365; and if not a step 369 determines if the image toggle was enabled in step 359. If in step 359 the toggle had been enabled, a step 371 enables the toggle interrupt routine again and operations proceed to a step 375; and if not operations go directly from step 369 to step 375. Step 375 allows the '+' or 'x' to be moved as explained above in connection with step 365.

A step 377 then senses if an exit flag is set. If it is not set the operations go to step 357. When both images have their respective software marks or reference points put in place, the operator in a step 357 presses the return or space bar key, and then a step 373 sets an exit flag.

If in step 377 the exit flag is sensed to be set, a step 379 aligns the software '+' with the software 'x' by shifting image 2 by vertical and horizontal sliding operations until the two marks intersect or coincide. For example, if the "x" and the "+" are at coordinates X1, Y1 on Image 1 and X2, Y2 on Image 2, then the sliding operations move Image 2 in the horizontal X direction by an amount X1-X2 and move Image 2 in the vertical Y direction by an amount Y1-Y2. Inside the image memory contents are copied by hardware move operations in groups of 8 pixels in a row at a time into new addresses resulting from the move in the Y direction or the X direction. The portion of image 2 which is no longer used due to the alignment operation is blacked out. It is contemplated that in a further optional operation, an image rotation of one of the images relative to the other is used to perfectly superimpose corresponding parts of one image on each other if this is not already accomplished by vertical and horizontal operations. Thus shifting or sliding operations can include a rotational aspect as well as a linear aspect. After step 379 point K is reached.

Selection of the patient identification function key F9 causes a branch from step 57 of FIG. 2 to a path I of FIG. 12. Operations of FIG. 12 proceed to a step 401 which is a prompt for an input of a patient identification. At this point the operator specifies an 8 character identifier to be used for the functions described in FIG. 7. When a new identifier is specified, a step 403 resets the exchange flag and path E is initialized so it will move the display into the buffer rather than exchanging the display with the buffer. After step 403 is completed a step 405 unprotects images 1 and 2 and a step 406 sets the New Patient NP flag. The function F9 may be escaped from (as may any other) by depressing the return key while holding a shift key in the depressed state.

Figure 13:
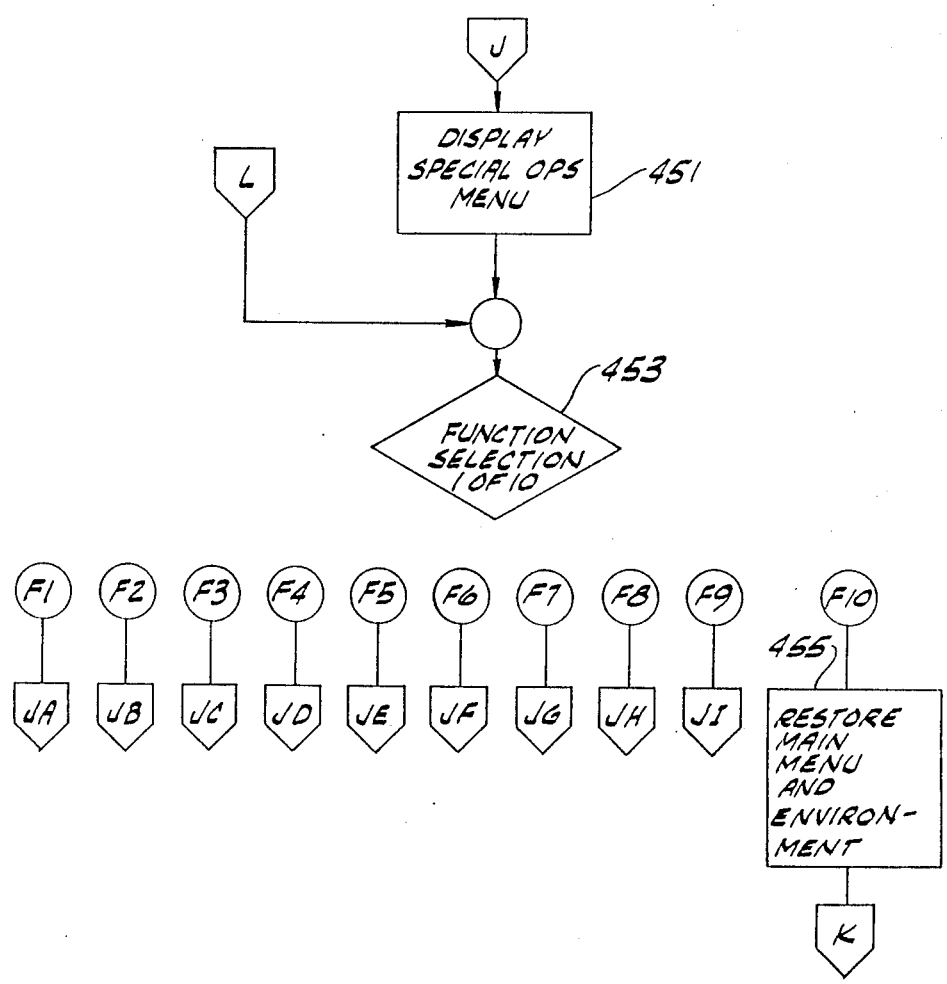
FIG. 13 is a flowchart of a special operations menu selected from the main menu of FIG. 2.

Selection of function key F10 causes the operations to branch to path J shown in FIG. 13. The operations proceed to a step 451 which selects and displays the "SPECIAL OPERATIONS" menu level. Step 451 redefines function keys F1-F10. If the operator selects function key F10, a step 455 will restore main menu and the corresponding environment and the computer is at step 57.

Figure 14:
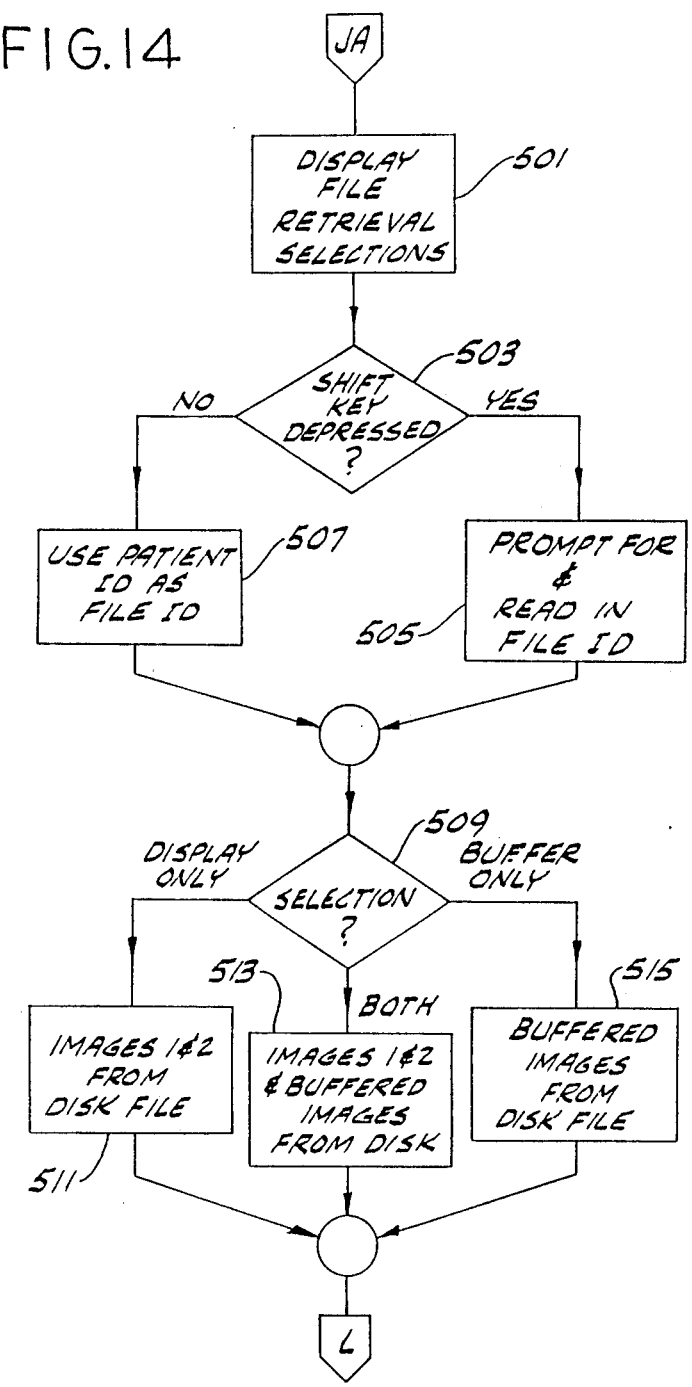
FIG. 14 is a flowchart of file retrieval operations in the special operations menu of FIG. 13.

If function F10 is chosen in a step 57 and subsequently F1 is chosen, in FIG. 13, operations proceed to a step 501, as in FIG. 14, at which the file retrieval selections are displayed. A step 503 then senses if the shift key is depressed, if it is not then the patient identification is used as the file identification in a step 507. If step 503 senses that the shift key is depressed, the software will prompt the operator to input a file identification in a step 505. When either step 505 or 507 is completed the operations proceed to a step 509, which determines a location from which the selected files are to be retrieved, the selections being DISPLAY, BUFFER, and BOTH. Steps 511 and 515 respond to the selection in step 509 of DISPLAY and BUFFER respectively and a step 513 responds to a selection of BOTH in step 509. If step 511 is activated, both images 1 and 2 from the disk file are retrieved. Analogously, step 515 retrieves the buffered images from the disk. Step 513 retrieves images 1 and 2 and buffered images from disk.

Figure 15:
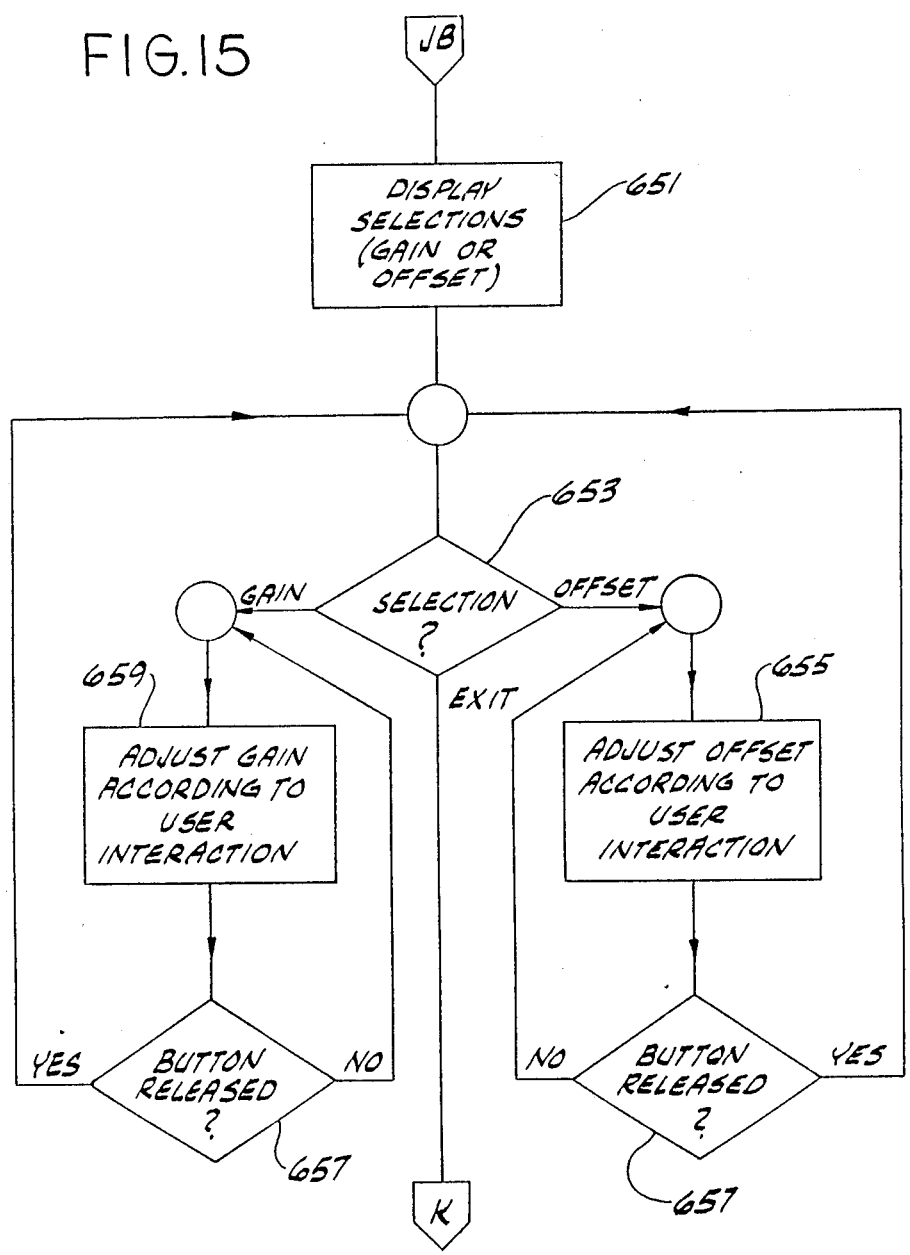
FIG. 15 is a flowchart of gain and offset operations in the special operations menu of FIG. 13.

In FIG. 13 selection of gain/offset function F2 on the Special Operations Menu causes a branch from step 453 to path JB of FIG. 15. Gain corresponds to display contrast. Offset corresponds to display brightness. An image negative on the display can also be produced by this function. Operations of FIG. 15 proceed to a step 651 which displays options or selections entitled GAIN, OFFSET and EXIT. A message is displayed as follows:

ADJUST GAINS AND OFFSETS
DEPRESS: F1 TO ADJUST IMAGE 1;
F2 TO ADJUST IMAGE 2;
SPACE BAR TO EXIT.
UP-DOWN CURSOR MODIFIES GAIN
RT-LEFT CURSOR MODIFIES OFFSET

To adjust the offset, operator selects the OFFSET option of a step 653, from which operations branch to a step 655 where the offset is adjusted according to user interaction. The offset is a brightness adjustment made by depressing and holding the appropriate button or key while adjusting with cursor control. A similar adjustment of the gain or contrast is accomplished in a step 659. Vertical cursor motion adjusts gain with more positive gain in the upward direction. Horizontal cursor motion adjusts offset with the move positive to the right. After the gain and/or offset has been adjusted a test subroutine step 657 senses if the appropriate button or key has been released. If the button has been released then operations go from test subroutine step 657 to step 653 for further selection or exit to point K. If the button has not been released, then operations go back to step 655 or to step 659 depending on whether the gain or offset is being further adjusted. Neutral adjustment (offset; gain of 1) may be achieved by depressing the center mouse button or the space bar while the image selector (left or F1 for image 1; right or F2 for image 2) is depressed. When the gain and/or offset has been properly adjusted the EXIT option is selected.

If the operator selects function key F3 of step 453 of FIG. 13 operations proceed to a path JC. Path JC will then display a list of all the images currently stored on the hard disk 27. If functions F4 or F5 are chosen operations will move to a path JD or JE respectively. Path JD transfers the selected image date from hard disk 27 to portable disk 33. Path JE performs the opposite function by transferring selected image data from portable disk 33 to hard disk 27. If the operator selects F6, the computer will prompt the operator to rename the selected stored image(s). Function F7 if selected by the operator, deletes any selected stored image(s) from memory (hard disk or portable disk). Function F8 prompts the operator to input the time and date.

Figure 16:
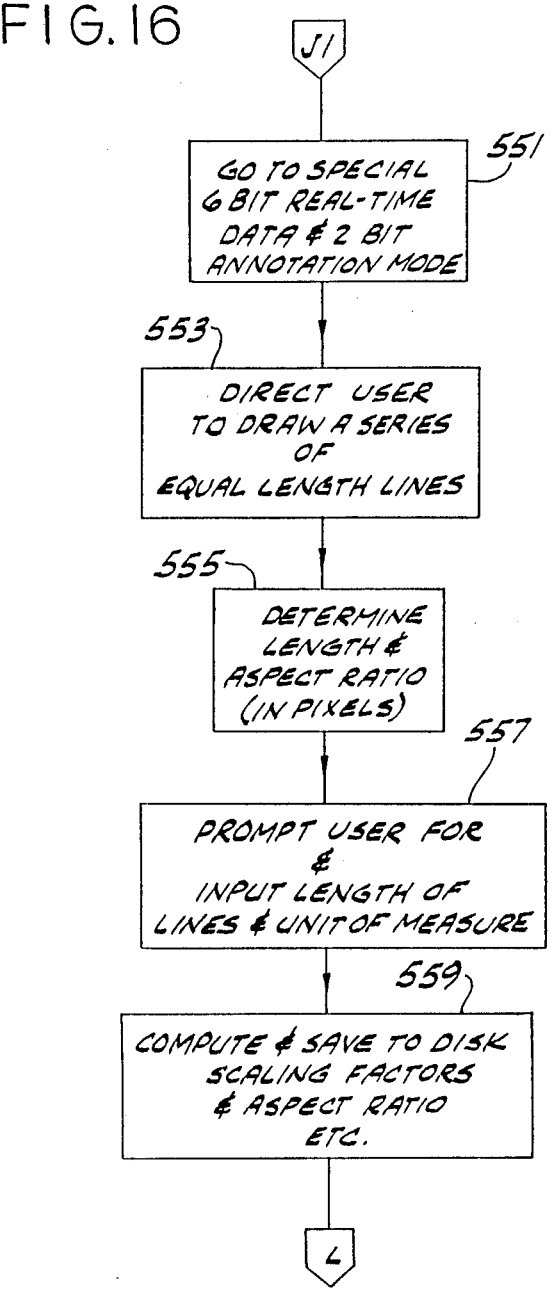
FIG. 16 is a flowchart of operations for computing scaling factors and aspect ratio in the special operations menu of FIG. 13.

If function F10 is chosen in a step 57 and subsequently F9 is chosen, in FIG. 13, operations proceed to a path JI as in FIG. 16 to calibrate the ruler to the camera optics. Operations proceed to a step 551 and the computer converts to a 6 bit real-time data and 2 bit anotation made to prepare the software for calibration. After the software mode is properly established step 553 directs operator to draw a series of equal length lines. The software then, in a step 555, determines the length and aspect ratio, in pixels, of the lines drawn in step 553. The operations then proceed to a step 557, which prompts the operator to input the length of the lines and the unit of measure according to the following display message:

MOVE THE CURSOR TO ONE END OF A REFERENCE LINE AND PUSH F2. NEXT MOVE TO THE OTHER END AND DO THE SAME. REPEAT THIS ON ANOTHER LINE OF THE SAME LENGTH NOT PARALLEL TO THE FIRST.
REPEAT THIS PROCEDURE WITH UP TO 20 LINE PAIRS OF EQUAL LENGTH, AND AN AVERAGE WILL BE COMPUTED.

-continued
DEPRESSING F1 WILL DELETE THE LAST POINT ENTERED.
DEPRESS THE SPACE-BAR BUTTON WHEN ALL PAIRS ARE ENTERED OR TO ENTER SCALE FACTORS ON THE KEYBOARD.
ENTER UNITS:
ENTER NUMBER OF PIXELS PER . . .
HORIZONTALLY:
VERTICALLY:

The scaling factors, aspect ratios and units of measure are saved to the disk in a step 559.

SUGGESTED PROCEDURE

The following is a suggested procedure to use for acquiring and comparing images:

A. If the software ruler provided is to be used, it must be initially calibrated to the optical system. Calibration need only be performed once if the optical system does not change, however any changes in optical power settings (zoom) will require the ruler to be rescaled (see RULER CALIBRATION).

B. Select F9 and enter an 8 character identifier for the files which will be created for reference and backup. The following characters are allowed:
   1. Any upper or lower case alphabetic character (the system will not differentiate between upper and lower);
   2. Any digit 0-9;
   3. The characters ! @ # $ %   & ( ) _ - { } ' ` ~;
   Any character other than the above will be replaced with the _ character.

C. Upon power-up both images 1 and 2 will be acquiring real-time camera data, i.e. neither should be 'protected' and input mode should be "REAL-TIME". When the desired reference image is present on the monitor, select F3 to FROZEN. The desired frozen reference will now be in image 1 and 2.

D. At this time select F5, "MOVE DISPLAY INTO BUFFER", to hold the reference for later use. Both images 1 and 2 will be moved into the buffer. This selection will now change to read "EXCHANGE DISPLAY WITH BUFFER" until a new patient/file identifier is selected.

E. When the move is complete (about 1 second) i.e. the selection stops flashing, select F3 to REAL-TIME input mode. This enables acquiring of a second reference image for alternative methods or positions.

F. As in step B, both images will be acquiring real-time camera data. When the desired second reference image is present on the monitor, again select F3 to FROZEN. The second reference will now be in both images 1 and 2.

G. Now make the selection F5 as in step C which now reads "EXCHANGE DISPLAY WITH BUFFER". The original reference will appear on the monitor, and both images 1 and 2 will be protected. The second reference (both images 1 and 2) is now in the buffer for later use. The original reference is now in the display (both images 1 and 2).

H. At this time both the buffer (the second reference) and the display (the first reference) should be saved to disk by selecting F6 and then making the appropriate sub-selection in order to protect against accidental erasure.

I. Both references are now in memory and on disk. F5 can be used to select between references. When ready to compare a reference with real-time camera images, bring the desired reference to the display using F5. Select F3 to REAL-TIME. This will un-protect image 1 which will now display real-time camera data. Select F4 to begin rapid alternation between the realtime image in image 1 and the reference image in image 2. The dwell time may be altered at this point to the desired flash rate. To 'pre-view' either image depress and hold F1 or F2 as appropriate.

J. To allow the desired positioning of frozen images to be done easily and quickly, make the selection F8, JUXTAPOSE IMAGE. This selection will prompt the operator to place software reference marks on both images 1 and 2. The computer will then move image 2 by horizontal and vertical operations with the reference marks until the respective images are merged.

K. Now select F5 to display the second reference and repeat the procedure described in H. When the second set of images is FROZEN, save both to disk using F6.

L. Return to step B, and continue.

The juxtapose operation of step J is further detailed as follows:

1. Press F8 to start JUXTAPOSE operation.

Note: In this operation, an identical, easily identifiable portion of one of the marker sutures is selected (this will be the reference suture) from each memory image and marked with a unique cursor. After completion of the cursor marking, the computer repositions image 2 over image 1 so that the marks are superpositioned.

2. Press and hold down the F1 Key to view the image in Memory 1. Use ARROW Keys to position the marker (a "+") to the chosen identification point.

3. Press F2 and view the image in Memory 2. Overlay the other marker (an "x") to the exact same position as the "+".

4. Press F1 and F2 alternately to verify the identical alignment of the markers in each image of the same suture.

5. When satisfied that the markers have been suitably positioned, Press the SPACEBAR. This will cause image 2 to juxtapose onto image 1 as these are flickered on the image screen.

The embodiment as discussed allows for manual alignment of a frozen image with a simultaneously displayed "live" image, and manual selection of a FREEZE option in order to obtain "before" and "after" comparisons in detail.

In a further improvement, automatic freeze is obtained as discussed next, when the images are sufficiently well aligned. First, provide for selection of a small Area of Interest (AOI) to reduce the amount of data which is processed. In the ophthalmic surgery application, the AOI is a single one of two guide stitches made on the eye by the surgeon. Second, the AOI of the "before" image is processed into a binary sub-image by thresholding. Third, the portion of the "live" image which falls in the AOI is similarly processed and compared to the "before" sub-image of each frame. If the comparison is favorable, the "after" image is frozen. The comparison is accomplished by assigning a value for each element of AOI according to whether the thresholded values of the images agree (1 if they do; −1 if they do not), summing the values, and comparing to another threshold.

FIG. 17 shows two inventively superimposed or alternating images of a human eye 701 with sclera 703, iris 705, pupil 707 and cornea 709. A first marking suture 711 applied to a limbus of cornea 709 coincides with itself in both images, as do two superimposed reference points 713' and 713" applied by operator on each image. An incision site 715 is bounded by the marking suture 711 and a second marking suture which shows up as two different suture images 717' and 717" due to its displacement in position during surgery. In other words, an interrupted line of sutures is imbedded in the surface, in or near the cornea, placed on each side and parallel to the line of the intended incision. These serve as measurement edges or points. An incision 719 between the two marking sutures is closed with stitches 721. A distance B between the two different images 717' and 717" of the same marking suture is measured in diopters equivalent of linear measurement in millimeters. A software ruler or measurement scale 725 is superimposed on the images so that the distance B is readily measured.

FIG. 18 is a sketch of Image 1 and Image 2 shown side by side in the drawing. Image 1 includes the images 711' and 717" of the first and second marking sutures respectively. Operator has superimposed a '+' reference point on the image 711+ of the first marking suture using the keyboard. Image 2 includes the images 711" and 717" of the first and second marking sutures respectively and the image 721 of the incision and stitches. Operator has superimposed a 'x' reference point on the image 711" of the first marking suture using the keyboard.

FIG. 19 shows the two images of FIG. 18 superimposed as they initially appear on display unit 15. The images are not yet in registry. The distance between the marking sutures is about 3 millimeters which occupies part of a 6×8 millimeter video field of view. Then the computer is programmed and activated to automatically bring the images into alignment or registry by causing Image 2 to slide or shift in the direction of an arrow 725 so that the '+' and 'x' reference points coincide and the images are aligned. When the shifting is accomplished, the aligned images of FIG. 17 are the result.

In this way the computer acts as means for transmitting representations of visual reference points under operator control to said display means for display on corresponding parts of the stored image and the present image respectively and for electronically aligning the two images so that the reference points coincide.

Figure 20:
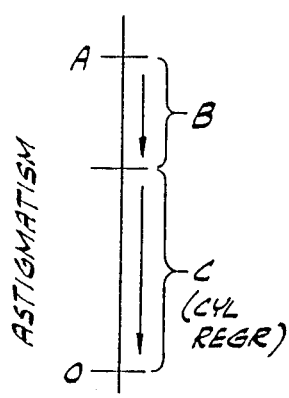
FIG. 20 is a sketch of a number line showing a desired relationship of pre-surgical astigmatism A, a distance B between corresponding points on the pre-surgical and post-surgical images of FIG. 17, and a cylindrical regression profile value C.

FIG. 20 shows a number line representing astigmatism A which is to be corrected, if possible, to zero. As an example, assume a patient has preoperative astigmatism of 3 diopters of minus cylinder axis 180. Further in the example, the marking sutures are found by using the measurement scale to be 0.15 millimeters (1.5 diopters) further apart after surgery than they were before surgery. Therefore, the value of B is 1.5 diopters. (That every diopter of change in astigmatism corresponds to 0.1 millimeter of displacement B is a rule of thumb accurate to within about 10% for the human eye.) If the value of cylinder regression (expansion of incision site) due to healing for the particular surgeon doing the surgery is 1.5 diopters, then the final value of astigmatism is $3-1.5-1.5=0$, and the astigmatism is completely corrected.

If the patient has no astigmatism then the marking sutures should be placed 0.15 millimeters closer together after surgery than were before surgery to compensate for the 1.5 diopters of cylinder regression for that individual surgeon. The arithmetic is $0 - (-1.5) - 1.5 = 0$.

In general, the astigmatism correction procedure is given by equation (1):

$$A - B - C = 0 \qquad (1)$$

where A is preoperative astigmatism of the individual patient (suitably measured by a keratometer), B is the difference by subtracting a pre-surgical distance D1 (FIG. 18) of marking sutures from a post-surgical distance D2 of marking sutures, and C is the cylinder regression value for the individual surgeon.

Two classes of astigmatism called With-the-Rule astigmatism and Against-the-Rule astigmatism are measured in diopters and are regarded as values of A having opposite algebraic signs for purposes of equation (1). With-the-Rule astigmatism is also known as any of the following: (A) minus cylinder axis 180; (B) positive cylinder axis 90; (C) astigmatism in which the steeper meridian (smaller radius of curvature) is vertical (at axis 90°); (D) astigmatism in which the horizontal (180°) meridian is flatter. Against-the-Rule astigmatism is also known as any of the following: (A) positive cylinder at axis 180; (B) minus cylinder at axis 90; (C) astigmatism in which the steeper meridian (smaller radius of curvature) is horizontal (at axis 180°); (D) astigmatism in which the vertical (90°) meridian is flatter. In cataract surgery the incision is typically made above the cornea. Increasing the marker distance (B positive) there makes the vertical meridian flatter, and decreasing the marker distance (B negative) makes it steeper. The term diopters (units of 1/meter) refers to the reciprocal of optical lens focal length in meters. Diopters of astigmatism refers to the excess of the diopters of the steeper meridian over the diopters of the other meridian. A sphere has zero astigmatism. Minus cylinder axis 180 (With-the-Rule astigmatism) has a positive sign of A herein.

A cylinder regression profile is a numerical value that represents an average postoperative change in astigmatism of patients of a particular surgeon and technique being used. The cylinder regression profile value is a function of the type of suture used, the depth of suture placement, and the particular suturing method utilized, and varies substantially from surgeon to surgeon. More specifically, the cylinder regression value is a function of suture type (such as 9-0 diameter or 10-0 diameter monofilament black suture), whether the suture is interrupted (separate individual stitches) or uninterrupted (such as running shoestring), the suture density and how far apart sutures are, the suture depth, and wound data identifying whether the surgical limbus is on the corneal or scleral side, and the thickness of a scleral flap in surgery. The change in astigmatism due to healing is tabulated according to the variables listed above. A next step is to compute an arithmetic average of the values of change in astigmatism after all of the surgeons's operations having identical identifying data. The average so computed is the cylinder regression value for the individual surgeon. The cylinder regression value generally decreases as the surgeon increases in experience and skill.

A further consideration of equation (1) helps to emphasize a distinct difference in approach of some embodiments of the inventive methods compared to prior art surgical techniques.

In a prior art approach, a keratometer is used not only to determine the pre-surgical astigmatism A but also to roughly determine a post-surgical astigmatism corresponding in value to the difference $A - B$ in equation (1). In the prior art, however, the value of B was not measured. The sutures stitching the incision were adjusted to reduce the post-surgical astigmatism measured by the keratometer. The value of the cylinder regression is believed to have been unavailable to or not considered by the individual surgeon. Because the value of corneal curvature determined by the keratometer depends on intracorneal pressure which the surgeon can only roughly restore by injection of fluid into the anterior chamber of the eye, the postoperative astigmatism value so determined is relatively uncertain. As a result, the patient's astigmatism may be only partially corrected, if at all.

In an embodiment of a method of the invention, the cylinder regression value is predetermined on the basis of the individual surgeon's records, and the individual patient's pre-surgical astigmatism is measured with the keratometer. Since A and C are knowns, equation (1) is rearranged to show $$B = A - C \qquad (2)$$

In words, equation (2) states that astigmatism is corrected by adjusting, for example, an initial triple-throw knot on the incision on each suture (or in the running shoestring) thereon so that the value of B is equal to a predetermined value $A - C$. The value $A - C$ is the difference of the patient's preoperative astigmatism and the surgeon's cylinder regression value. In other words, this method is an example of steps including predetermining a first value representing a surgeon's cylinder regression profile and a second value representing a patient's astigmatism, and adjusting the closure of the incision to make the magnitude of the difference between the pre-surgical distance and the post-surgical distance equal to the magnitude of the difference of the value representing the patient's astigmatism less the surgeon's cylinder regression profile value, or any other appropriate function of the values of astigmatism and cylinder regression.

The reapposition monitoring apparatus herein described is advantageously suited to measuring the value of B and remeasuring B while adjustments in the triple-throw knot are made as the surgery itself is completed prior to tying the stitches. The sutures are thus readjusted as necessary to accomplish the desired tissue displacement and the knots are locked by placing two or three single throws on top of the triple throw adjustable knot. The value of B is either positive or negative depending on whether the post-surgical distance is greater or less than the pre-surgical distance respectively. Often after adjustment of stitches, the post-surgical distance is less than the pre-surgical distance and B is negative (($A - B$) exceeding A) for example. The surgeon's post-surgical use of the keratometer now takes on the roles of validation and of gathering data to update the cylinder regression value for a later operation on a different patient.

Advantageously, the reapposition monitor described hereinabove is used in cataract and/or refractive surgery, displaying and measuring the reapposition or alteration of position of the corneal, scleral or corneoscleral tissues resulting from surgery. The surgeon can maintain or impose a predetermined change in the wound apposition to maintain or change the degree of corneal astigmatism or lack of astigmatism. It identifies undisturbed pre-surgical tissue sites adjacent to and along the intended surgical incision with precise, optically visible indicators, marks, or markers. It displays, records and measures the distances between apposed indicators or marks placed at points or as a marking suture line along each side of the intended incision. The apparatus redisplays, remeasures and records the corresponding distances during the surgical procedure, especially just after closing the incision to determine the change B of the relative pre-incision versus post-incision distance. Further the apparatus redisplays the pre-surgical image and superimposes this either simultaneously or sequentially with the real-time post-surgical image. The images may be fused into one composite image or toggled at an adjustable rate to enhance the differences between the images. A measuring scale is calibrated as required and positioned in any part of the image field or along any angle, and is superimposed on either or both images for measurement purposes. The comparative measurements are used by ophthalmologists, for instance, to calculate and predict the changes from the preoperative corneal power and/or astigmatism resulting from a planned or unplanned change in the distance between marks.

Figure 21:
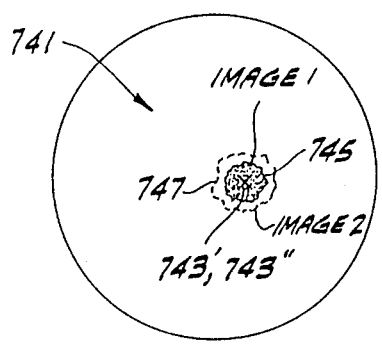
FIG. 21 is a sketch of a microscopic field of view showing two alternating images of a crater where the optic nerve joins the retina of the eye of FIG. 17, and illustrating a glaucoma condition.

A further application contemplated for a video monitor of the invention is monitoring for glaucomatous cupping. As illustrated in FIG. 21, the field of view 741 of a microscope is in an early examination directed to the optic nerve cup 745 and stored as Image 1. In a subsequent examination, the procedure is repeated and the image is stored as Image 2. Image 2 shows that the nerve cup is a crater 747 in which glaucoma is progressively pinching off the optic nerve to produce blindness. Reference points 743' and 743" are superimposed on the center of the cup in Image 1 and Image 2, and the video monitor computer automatically aligns the images for ready comparison and measurement of the progress of the glaucoma condition.

Still other applications contemplated for the monitoring apparatus include monitoring of retinopathy, neurovascular changes, and other changes in biological tissues of all types.

A method which alternates images advantageously permits the user to distinguish between the images at the longer dwell times. As the dwell time is decreased, the images become essentially superimposed as perceived by the user, with only some flicker remaining. In another embodiment images are superimposed by routing electrical representations of the Image 1 and Image 2 to different RGB (red-green-blue) color guns of a color video picture tube of display unit 15 so that they are superimposed in contrasting colors. A corresponding superimposing operation can also be accomplished in monochrome. Alternating display and selectable image functions are included in the menu of functions.

Given the power of the computer there are other improvements that can be added. As an example, a graphic representation of intensity of a slice of video intensity along the measurement scale can be used to visually derive centers of marks (e.g., the anterior and posterior markers) and then enable measurement of the difference B. Further, the computer through additional processing can determine the centers of the measurement marks and automatically determine and digitally display the difference B.

It is apparent that various embodiments of the inventive monitoring apparatus and methods can be implemented entirely with hardware, or by hardware with firmware components, as well as in a general purpose programmed computer with associated input and output outboard hardware as illustrated herein.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Video monitoring apparatus for use in an application in which changes in relative spatial relationship of features of a biological tissue are to be observed, the apparatus comprising:

video camera means for electronically producing a first image of the tissue and also electronically developing a subsequent image of the tissue after a period of time;

video means for displaying a representation of an image of the tissue derived from said camera means; and means connected to said camera means and to said displaying means for electronically storing a representation of the first image of the tissue, and for transmitting the representation of the first image of the tissue to the displaying means with a representation of the subsequent image of the tissue so that the first and subsequent images of the tissue appear superimposed and any differences in the relative spatial relationship of features of the tissue in the images of the tissue are readily observed.

2. Video monitoring apparatus as set forth in claim 1 wherein said means for storing and transmitting includes means for alternately transmitting the image representations and establishing dwell times of display for the first and subsequent images.

3. Video monitoring apparatus as set forth in claim 1 wherein said means for storing and transmitting includes means for sensing an operator selection of a particular one of the images and for holding only the selected image on the display by temporarily stopping the transmission of any other image.

4. Video monitoring apparatus as set forth in claim 1 wherein said means for storing and transmitting includes means for transmitting a representation of a measuring scale to superimpose the measuring scale on the display screen, whereby differences in position of features of the images are measurable.

5. Video monitoring apparatus as set forth in claim 1 wherein said means for storing and transmitting includes means for transmitting representations of visual reference points under operator control to said display means for display on the stored image and the present image respectively.

6. Video monitoring apparatus as set forth in claim 1 wherein said means for storing and transmitting includes means for transmitting representations of visual reference points under operator control to said display means for display on corresponding parts of the stored image and the present image respectively and for electronically aligning the two images so that the reference points coincide.

7. Video monitoring apparatus as set forth in claim 1 wherein said means for storing and transmitting includes means for electronically sliding one of the first and subsequent images relative to the other.

8. Video monitoring apparatus as set forth in claim 1 wherein said camera means includes a microscope.

9. Video monitoring apparatus as set forth in claim 1 wherein the subsequent image is a changing real-time image of the tissue and the first image of the tissue appears superimposed with the changing real time image of the tissue.

10. Reapposition monitoring apparatus for use in surgery wherein the position of pre-surgical tissue is to have a predetermined relationship to the position of the tissue after surgical incision and during subsequent closure of the incision, the apparatus comprising:
camera means for electronically producing an image of the tissue in its presurgical position and also electronically producing a subsequent surgical image when the incision is being closed;
means connected to said camera means for electronically storing a representation of the pre-surgical image of the tissue; and
means for displaying a representation of an image from said means for electronically storing;
said means for electronically storing including means for alternately transmitting the representation of the presurgical image to the displaying means with a representation of the subsequent surgical image during closure of the incision, thereby allowing visual comparison of the presurgical image with the subsequent surgical image.

11. Reapposition monitoring apparatus as set forth in claim 10 wherein said means for storing and transmitting includes means for transmitting representations of visual reference points under operator control to said display means for display on the stored image and the present image respectively.

12. Reapposition monitoring apparatus as set forth in claim 10 wherein said means for transmitting includes means for sending representations of visual reference points under operator control to said display means for display on corresponding parts of the stored image and the present image respectively and for electronically aligning the two images so that the reference points coincide.

13. Reapposition monitoring apparatus as set forth in claim 10 wherein said means for transmitting includes means for sending representations of visual reference points under operator control to said display means for display on corresponding parts of the stored image and the present image respectively, for electronically aligning the two images so that the reference points coincide and for superimposing a representation of a measuring scale on the display screen, whereby differences in position of features of the images are measurable.

14. A method of monitoring for changes in relative spatial relationship of features of a biological tissue, comprising the steps of:
electronically aligning a first video image of the tissue with a second video image of the same tissue after a period of time has elapsed;
automatically superimposing the first and second video images for display purposes to allow the differences between the first and second images of the tissue to be easily distinguished; and
electronically superimposing and moving a measurement scale visually on the display, whereby differences in position of features of the images of the tissue are measurable.

15. A method of monitoring for changes in relative spatial relationship of features of a biological tissue, comprising the steps of:
electronically aligning a first video image of the tissue with a second video image of the same tissue after a period of time has elapsed;
automatically superimposing the first and second video images for display purposes to allow the differences between the first and second images of the tissue to be easily distinguished; and
electronically positioning visual reference points under operator control for display on the images of the tissue respectively.

16. A method of monitoring for changes in relative spatial relationship of features of a biological tissue, comprising the steps of:
electronically aligning a first video image of the tissue with a second video image of the same tissue after a period of time has elapsed;
automatically superimposing the first and second video images for display purposes to allow the differences between the first and second images of the tissue to be easily distinguished;
electronically positioning visual reference points under operator control for display on corresponding parts of the images of the tissue respectively; and
electronically aligning the two images so that the reference points coincide.

17. A reapposition monitoring method for use in surgery wherein the position of pre-surgical tissue is to have a predetermined relationship to the position of the tissue after surgical incision and subsequent closure of the incision, the method comprising the steps of:
prior to surgery marking a surgical area on the patient with marks located on opposite sides of an incision site and separated by a pre-surgical distance;
electronically producing and storing a pre-surgical image of the marks and the incision site;
electronically producing a post-surgical image of the marks and the incision site and alternately displaying the postsurgical and pre-surgical images on a display;
measuring on the images a value of difference between a pre-surgical distance between the marks and a post-surgical distance between the marks; and
adjusting the closure of the incision until the value of difference between the pre-surgical distance and the postsurgical distance is substantially equal to a predetermined value.

18. A method as set forth in claim 17 further comprising predetermining a first value representing a surgeon's cylinder regression profile and a second value representing a patient's astigmatism, and wherein the adjusting step includes making the value of difference between the pre-surgical distance and the post-surgical distance equal to a value which is a function of the values of the surgeon's cylinder regression and the patient's astigmatism.

19. A method as set forth in claim 17 further comprising predetermining a first value representing a surgeon's cylinder regression profile and a second value representing a patient's astigmatism, and wherein the adjusting step includes making the magnitude of the difference between the pre-surgical distance and the postsurgical distance equal to the magnitude of the difference of the value representing the patient's astigmatism less the surgeon's cylinder regression value.

20. A method as set forth in claim 17 further comprising electronically superimposing a visual reference point on a feature of the pre-surgical image and then superimposing a second visual reference point on the same feature of the post-surgical image and then electronically sliding one of the images relative to the other to make the reference points coincide, whereby the difference between the pre-surgical distance and post-surgical distance is readily measured in the measuring step.

* * * * *